(12) United States Patent
Lichtenstein et al.

(10) Patent No.: US 11,033,392 B2
(45) Date of Patent: Jun. 15, 2021

(54) SYSTEM FOR IMPROVING DIASTOLIC DYSFUNCTION

(75) Inventors: Samuel Victor Lichtenstein, Vancouver (CA); Daniel Gelbart, Vancouver (CA); William Gelbart, Vancouver (CA)

(73) Assignee: KARDIUM INC., Burnaby (CA)

( * ) Notice: Subject to any disclaimer, the term of this patent is extended or adjusted under 35 U.S.C. 154(b) by 934 days.

(21) Appl. No.: 12/904,885

(22) Filed: Oct. 14, 2010

(65) Prior Publication Data

US 2011/0087203 A1 Apr. 14, 2011

Related U.S. Application Data

(63) Continuation of application No. 11/497,309, filed on Aug. 2, 2006, now Pat. No. 7,837,610.

(51) Int. Cl.
*A61F 2/24* (2006.01)

(52) U.S. Cl.
CPC .................................. *A61F 2/2487* (2013.01)

(58) Field of Classification Search
CPC ...... A61B 2017/00243; A61B 17/0057; A61B 2017/00575; A61B 2017/00592; A61B 17/12122; A61B 17/12172; A61B 18/1492; A61B 2017/12095; A61B 2018/00267; A61B 2017/00623; A61B 2018/00351; A61F 2/2487; A61F 2/2478
USPC ............. 606/191, 298; 600/16, 37; 623/904
See application file for complete search history.

(56) References Cited

U.S. PATENT DOCUMENTS

| | | | |
|---|---|---|---|
| 566,521 A | 8/1896 | Leger | |
| 3,132,438 A | 5/1964 | Ward et al. | |
| 4,041,955 A | 8/1977 | Kelly et al. | 128/419 P |
| 4,085,744 A | 4/1978 | Lewis et al. | |
| 4,114,202 A | 9/1978 | Roy et al. | 3/1.5 |
| 4,164,046 A | 8/1979 | Cooley | 3/1.5 |
| 4,225,148 A | 9/1980 | Anderson | |

(Continued)

FOREIGN PATENT DOCUMENTS

| | | |
|---|---|---|
| EP | 0723467 B1 | 4/2002 |
| EP | 2082690 | 6/2012 |

(Continued)

OTHER PUBLICATIONS

Kuhn C, Werdan K. Hemodynamic monitoring. In: Holzheimer RG, Mannick JA, editors. Surgical Treatment: Evidence-Based and Problem-Oriented. Munich: Zuckschwerdt; 2001. Available from: https://www.ncbi.nlm.nih.gov/books/NBK6895/.*

(Continued)

*Primary Examiner* — Darwin P Erezo
*Assistant Examiner* — Erin L Colello
(74) *Attorney, Agent, or Firm* — Rossi, Kimms & McDowell LLP

(57) ABSTRACT

An elastic structure is introduced percutaneously into the left ventricle and attached to the walls of the ventricle. Over time the structure bonds firmly to the walls via scar tissue formation. The structure helps the ventricle expand and fill with blood during the diastolic period while having little affect on systolic performance. The structure also strengthens the ventricular walls and limits the effects of congestive heart failure, as the maximum expansion of the support structure is limited by flexible or elastic members.

49 Claims, 5 Drawing Sheets

(56) References Cited

U.S. PATENT DOCUMENTS

| | | | |
|---|---|---|---|
| 4,240,441 A | 12/1980 | Khalil | 128/692 |
| 4,261,342 A | 4/1981 | Aranguren Duo | |
| 4,263,680 A | 4/1981 | Reul et al. | 3/1.5 |
| 4,273,128 A | 6/1981 | Lary | |
| 4,411,266 A | 10/1983 | Cosman | |
| 4,490,859 A | 1/1985 | Black et al. | 3/1.5 |
| 4,527,554 A | 7/1985 | Klein | |
| 4,543,090 A | 9/1985 | McCoy | 604/95 |
| 4,699,147 A | 10/1987 | Chilson et al. | |
| 4,770,187 A | 9/1988 | Lash et al. | |
| 4,794,912 A | 1/1989 | Lia | 128/4 |
| 4,850,957 A | 7/1989 | Summers | 604/22 |
| 4,887,613 A | 12/1989 | Farr et al. | |
| 4,890,602 A | 1/1990 | Hake | 128/4 |
| 4,890,612 A | 1/1990 | Kensey | 606/213 |
| 4,893,613 A | 1/1990 | Hake | 128/4 |
| 4,895,166 A | 1/1990 | Farr et al. | |
| 4,921,499 A | 5/1990 | Hoffman et al. | 623/16 |
| 4,942,788 A | 7/1990 | Farr et al. | |
| 4,979,514 A | 12/1990 | Sekii et al. | |
| 4,994,698 A | 2/1991 | Kliman et al. | |
| 4,998,933 A | 3/1991 | Eggers et al. | |
| 5,021,059 A | 6/1991 | Kensey et al. | 606/213 |
| 5,026,384 A | 6/1991 | Farr et al. | |
| 5,039,894 A | 8/1991 | Teter et al. | |
| 5,047,047 A | 9/1991 | Yoon | 606/216 |
| 5,100,418 A | 3/1992 | Yoon et al. | 606/139 |
| 5,104,399 A | 4/1992 | Lazarus | 623/1 |
| 5,122,137 A | 6/1992 | Lennox | 606/40 |
| 5,127,902 A | 7/1992 | Fischell | |
| 5,156,151 A | 10/1992 | Imran | |
| 5,156,609 A | 10/1992 | Nakao et al. | |
| 5,174,299 A | 12/1992 | Nelson | |
| 5,176,693 A | 1/1993 | Pannek, Jr. | |
| 5,178,620 A | 1/1993 | Eggers et al. | |
| 5,192,291 A | 3/1993 | Pannek, Jr. | |
| 5,192,314 A | 3/1993 | Daskalakis | 623/3 |
| 5,201,316 A | 4/1993 | Pomeranz et al. | |
| 5,228,442 A | 7/1993 | Imran | |
| 5,242,386 A | 9/1993 | Holzer | |
| 5,242,456 A | 9/1993 | Nash et al. | |
| 5,245,987 A | 9/1993 | Redmond et al. | |
| 5,258,000 A | 11/1993 | Gianturco | 606/151 |
| 5,279,299 A | 1/1994 | Imran | |
| 5,293,869 A | 3/1994 | Edwards et al. | |
| 5,312,435 A | 5/1994 | Nash et al. | 606/213 |
| 5,312,439 A | 5/1994 | Loeb | 607/2 |
| 5,317,952 A | 6/1994 | Immega | |
| 5,320,632 A | 6/1994 | Heidmueller | 606/144 |
| 5,341,807 A | 8/1994 | Nardella | |
| 5,345,936 A * | 9/1994 | Pomeranz | A61B 5/0422 |
| | | | 600/374 |
| 5,364,408 A | 11/1994 | Gordon | 606/144 |
| 5,366,443 A | 11/1994 | Eggers et al. | 604/114 |
| 5,366,459 A | 11/1994 | Yoon | 606/151 |
| 5,368,601 A | 11/1994 | Sauer et al. | 606/144 |
| 5,374,275 A | 12/1994 | Bradley et al. | |
| 5,375,612 A * | 12/1994 | Cottenceau | A61F 2/01 |
| | | | 128/899 |
| 5,379,773 A | 1/1995 | Hornsby | |
| 5,383,887 A * | 1/1995 | Nadal | A61F 2/01 |
| | | | 606/198 |
| RE34,866 E | 2/1995 | Kensey et al. | |
| 5,390,664 A | 2/1995 | Redmond et al. | |
| 5,417,698 A | 5/1995 | Green et al. | |
| 5,419,767 A | 5/1995 | Eggers et al. | |
| 5,423,859 A | 6/1995 | Koyfman et al. | |
| 5,450,860 A | 9/1995 | O'Connor | 128/898 |
| 5,451,235 A * | 9/1995 | Lock | A61B 17/0057 |
| | | | 128/899 |
| 5,454,834 A | 10/1995 | Boebel et al. | |
| 5,462,561 A | 10/1995 | Voda | |
| 5,478,353 A | 12/1995 | Yoon | 606/213 |
| 5,496,267 A | 3/1996 | Drasler et al. | |
| 5,507,811 A | 4/1996 | Koike et al. | |
| 5,531,760 A | 7/1996 | Alwafaie | 606/216 |
| 5,557,967 A | 9/1996 | Renger | |
| 5,558,091 A * | 9/1996 | Acker et al. | 600/424 |
| 5,575,810 A * | 11/1996 | Swanson | A61B 18/1492 |
| | | | 607/119 |
| 5,593,424 A | 1/1997 | Northrup, III | 606/232 |
| 5,598,848 A | 2/1997 | Swanson et al. | |
| 5,634,942 A * | 6/1997 | Chevillon | A61F 2/01 |
| | | | 606/194 |
| 5,645,566 A | 7/1997 | Brenneman et al. | |
| 5,662,587 A | 9/1997 | Grundfest et al. | |
| 5,681,308 A | 10/1997 | Edwards et al. | |
| 5,681,336 A | 10/1997 | Clement et al. | |
| 5,687,723 A | 11/1997 | Avitall | |
| 5,690,649 A | 11/1997 | Li | |
| 5,697,285 A | 12/1997 | Nappi et al. | |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,730,127 A | 3/1998 | Avitall | |
| 5,752,965 A | 5/1998 | Francis et al. | |
| 5,762,066 A | 6/1998 | Law et al. | |
| 5,769,846 A | 6/1998 | Edwards et al. | |
| 5,782,239 A | 7/1998 | Webster, Jr. | |
| 5,782,861 A | 7/1998 | Cragg et al. | 606/216 |
| 5,782,879 A | 7/1998 | Rosborough et al. | |
| 5,800,495 A | 9/1998 | Machek et al. | 607/116 |
| 5,824,066 A | 10/1998 | Gross | 623/2 |
| 5,830,222 A * | 11/1998 | Makower | 606/159 |
| 5,836,990 A | 11/1998 | Li | 607/28 |
| 5,865,791 A | 2/1999 | Whayne et al. | 604/49 |
| 5,871,505 A | 2/1999 | Adams et al. | 607/5 |
| 5,876,343 A | 3/1999 | Teo | |
| 5,881,727 A | 3/1999 | Edwards | |
| 5,891,136 A | 4/1999 | McGee et al. | |
| 5,904,711 A | 5/1999 | Flom et al. | |
| 5,919,207 A | 7/1999 | Taheri | 606/219 |
| 5,921,924 A | 7/1999 | Avitall | |
| 5,935,075 A | 8/1999 | Casscells et al. | |
| 5,935,079 A | 8/1999 | Swanson et al. | |
| 5,941,251 A | 8/1999 | Panescu et al. | |
| 5,961,440 A * | 10/1999 | Schweich, Jr. | A61B 17/00234 |
| | | | 600/16 |
| 5,964,782 A | 10/1999 | Lafontaine et al. | 606/213 |
| 5,971,994 A | 10/1999 | Fritzsch | |
| 5,976,174 A | 11/1999 | Ruiz | |
| 5,980,473 A | 11/1999 | Korakianitis et al. | |
| 5,984,950 A | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,045,497 A * | 4/2000 | Schweich, Jr. | A61B 17/00234 |
| | | | 128/898 |
| 6,059,715 A * | 5/2000 | Schweich, Jr. | A61B 17/00234 |
| | | | 128/898 |
| 6,063,082 A * | 5/2000 | DeVore | A61B 17/3468 |
| | | | 606/170 |
| 6,074,417 A | 6/2000 | Peredo | |
| 6,074,418 A | 6/2000 | Buchanan et al. | |
| 6,077,214 A * | 6/2000 | Mortier | A61B 17/00234 |
| | | | 128/898 |
| 6,104,944 A | 8/2000 | Martinelli | 600/424 |
| 6,113,610 A | 9/2000 | Poncet | 606/139 |
| 6,123,702 A | 9/2000 | Swanson et al. | |
| 6,132,438 A | 10/2000 | Fleischman et al. | 606/139 |
| 6,138,043 A | 10/2000 | Avitall | |
| 6,142,993 A | 11/2000 | Whayne et al. | |
| 6,156,046 A | 12/2000 | Passafaro et al. | |
| 6,183,496 B1 | 2/2001 | Urbanski | |
| 6,203,554 B1 | 3/2001 | Roberts | 606/144 |
| 6,210,432 B1 | 4/2001 | Solem et al. | 623/1.15 |
| 6,214,032 B1 | 4/2001 | Loeb et al. | 607/1 |
| 6,217,573 B1 | 4/2001 | Webster | |
| 6,221,103 B1 | 4/2001 | Melvin | 623/3.1 |
| 6,221,104 B1 | 4/2001 | Buckberg et al. | 623/3.1 |
| 6,231,561 B1 | 5/2001 | Frazier et al. | |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |

(56) References Cited

U.S. PATENT DOCUMENTS

| | | | |
|---|---|---|---|
| 6,261,309 B1 | 7/2001 | Urbanski | |
| 6,266,550 B1 | 7/2001 | Selmon et al. | |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,308,091 B1 | 10/2001 | Avitall | |
| 6,332,864 B1 | 12/2001 | Schweich, Jr. et al. | 600/16 |
| 6,346,105 B1 | 2/2002 | Tu et al. | 606/41 |
| 6,358,258 B1 | 3/2002 | Arcia et al. | 606/139 |
| 6,358,277 B1 | 3/2002 | Duran | |
| 6,360,749 B1 | 3/2002 | Jayaraman | 128/898 |
| 6,379,366 B1 | 4/2002 | Fleischman et al. | 606/139 |
| 6,383,151 B1 | 5/2002 | Diederich et al. | |
| 6,389,311 B1 | 5/2002 | Whayne et al. | |
| 6,391,048 B1 | 5/2002 | Ginn et al. | 606/213 |
| 6,391,054 B2 | 5/2002 | Carpentier et al. | 623/2.37 |
| 6,402,680 B2 | 6/2002 | Mortier et al. | |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |
| 6,416,459 B1 | 7/2002 | Haindl | 600/37 |
| 6,432,115 B1 | 8/2002 | Mollenauer et al. | |
| 6,436,052 B1 | 8/2002 | Nikolic et al. | 600/529 |
| 6,450,171 B1 | 9/2002 | Buckberg et al. | 128/898 |
| 6,475,223 B1 | 11/2002 | Werp et al. | 606/108 |
| 6,485,409 B1 | 11/2002 | Voloshin et al. | |
| 6,485,489 B2 | 11/2002 | Teirstein et al. | |
| 6,506,210 B1 | 1/2003 | Kanner | 606/213 |
| 6,514,194 B2* | 2/2003 | Schweich, Jr. | A61B 17/00234 600/16 |
| 6,514,249 B1 | 2/2003 | Maguire et al. | |
| 6,529,756 B1 | 3/2003 | Phan et al. | |
| 6,537,198 B1 | 3/2003 | Vidlund et al. | 600/16 |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,582,447 B1* | 6/2003 | Patel | A61F 2/01 606/200 |
| 6,589,160 B2* | 7/2003 | Schweich, Jr. | A61B 17/00234 600/16 |
| 6,589,208 B2 | 7/2003 | Ewers et al. | 604/104 |
| 6,626,930 B1 | 9/2003 | Allen et al. | 606/213 |
| 6,632,238 B2 | 10/2003 | Ginn et al. | 606/213 |
| 6,662,034 B2 | 12/2003 | Segner et al. | 600/373 |
| 6,676,685 B2 | 1/2004 | Pedros et al. | |
| 6,681,773 B2* | 1/2004 | Murphy | A61B 17/0218 128/898 |
| 6,704,590 B2 | 3/2004 | Haldeman | |
| 6,723,038 B1 | 4/2004 | Schroeder et al. | 600/16 |
| 6,726,704 B1 | 4/2004 | Loshakove et al. | 606/213 |
| 6,726,716 B2 | 4/2004 | Marquez | 623/2.36 |
| 6,743,241 B2 | 6/2004 | Kerr | 606/144 |
| 6,746,471 B2* | 6/2004 | Mortier | A61B 17/00234 600/201 |
| 6,749,622 B2 | 6/2004 | McGuckin, Jr. et al. | 606/213 |
| 6,752,810 B1 | 6/2004 | Gao et al. | |
| 6,755,777 B2* | 6/2004 | Schweich, Jr. | A61B 17/00234 600/16 |
| 6,760,616 B2 | 7/2004 | Hoey et al. | 600/547 |
| 6,780,197 B2 | 8/2004 | Roe et al. | 606/213 |
| 6,797,001 B2 | 9/2004 | Mathis et al. | 623/2.37 |
| 6,800,090 B2 | 10/2004 | Alferness et al. | 623/2.36 |
| 6,824,562 B2 | 11/2004 | Mathis et al. | |
| 6,837,886 B2 | 1/2005 | Collins et al. | |
| 6,840,957 B2 | 1/2005 | DiMatteo et al. | |
| 6,852,076 B2* | 2/2005 | Nikolic | A61B 17/12022 600/37 |
| 6,855,143 B2 | 2/2005 | Davison et al. | 606/41 |
| 6,881,218 B2* | 4/2005 | Beyer | A61F 2/01 606/198 |
| 6,890,353 B2 | 5/2005 | Cohn et al. | 623/2.37 |
| 6,892,091 B1 | 5/2005 | Ben-Haim et al. | |
| 6,899,674 B2 | 5/2005 | Viebach et al. | 600/152 |
| 6,907,297 B2 | 6/2005 | Wellman et al. | |
| 6,908,478 B2 | 6/2005 | Alferness et al. | 623/1.11 |
| 6,913,576 B2 | 7/2005 | Bowman | |
| 6,918,903 B2 | 7/2005 | Bass | |
| 6,926,669 B1 | 8/2005 | Stewart et al. | |
| 6,941,171 B2 | 9/2005 | Mann et al. | |
| 6,942,657 B2 | 9/2005 | Sinofsky et al. | |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,010 B2 | 1/2006 | Francischelli et al. | |
| 6,989,028 B2 | 1/2006 | Lashinski et al. | 623/2.37 |
| 6,991,649 B2 | 1/2006 | Sievers | |
| 6,994,093 B2 | 2/2006 | Murphy et al. | 128/898 |
| 6,997,951 B2 | 2/2006 | Solem et al. | 623/2.37 |
| 7,001,383 B2 | 2/2006 | Keidar | |
| 7,025,776 B1 | 4/2006 | Houser et al. | 606/213 |
| 7,050,848 B2 | 5/2006 | Hoey et al. | 600/547 |
| 7,052,487 B2 | 5/2006 | Cohn et al. | 604/509 |
| 7,068,867 B2 | 6/2006 | Adoram et al. | |
| 7,101,395 B2 | 9/2006 | Tremulis et al. | |
| 7,141,019 B2 | 11/2006 | Pearlman | |
| 7,144,363 B2 | 12/2006 | Pai et al. | 600/167 |
| 7,160,322 B2 | 1/2007 | Gabbay | |
| 7,166,127 B2 | 1/2007 | Spence et al. | |
| 7,172,551 B2* | 2/2007 | Leasure | A61M 1/1072 600/16 |
| 7,177,677 B2 | 2/2007 | Kaula et al. | 600/546 |
| 7,186,210 B2 | 3/2007 | Feld et al. | 600/16 |
| 7,187,964 B2 | 3/2007 | Khoury | |
| 7,189,202 B2 | 3/2007 | Lau et al. | 600/37 |
| 7,276,044 B2 | 10/2007 | Ferry et al. | |
| 7,279,007 B2* | 10/2007 | Nikolic | A61B 17/12022 600/37 |
| 7,280,863 B2* | 10/2007 | Shachar | 600/424 |
| 7,300,435 B2 | 11/2007 | Wham et al. | 606/34 |
| 7,303,526 B2* | 12/2007 | Sharkey | A61B 17/12022 600/37 |
| 7,320,665 B2* | 1/2008 | Vijay | A61B 17/12022 600/16 |
| 7,335,196 B2 | 2/2008 | Swanson et al. | |
| 7,374,530 B2 | 5/2008 | Schaller | |
| 7,399,271 B2* | 7/2008 | Khairkhahan | A61B 17/12022 600/16 |
| 7,413,568 B2* | 8/2008 | Swanson | A61B 18/1492 606/41 |
| 7,431,726 B2 | 10/2008 | Spence et al. | |
| 7,452,325 B2 | 11/2008 | Schaller | |
| 7,452,375 B2 | 11/2008 | Mathis et al. | |
| 7,507,252 B2 | 3/2009 | Lashinski et al. | 623/2.37 |
| 7,513,867 B2* | 4/2009 | Lichtenstein | 600/37 |
| 7,582,051 B2 | 9/2009 | Khairkhahan et al. | |
| 7,611,534 B2 | 11/2009 | Kapadia et al. | |
| 7,674,276 B2 | 3/2010 | Stone et al. | |
| 7,704,277 B2 | 4/2010 | Zakay et al. | |
| 7,736,388 B2 | 6/2010 | Goldfarb et al. | |
| 7,738,967 B2 | 6/2010 | Salo | |
| 7,749,249 B2 | 7/2010 | Gelbart et al. | |
| 7,837,610 B2 | 11/2010 | Lichtenstein et al. | 600/16 |
| 7,869,854 B2* | 1/2011 | Shachar et al. | 600/374 |
| 7,873,402 B2* | 1/2011 | Shachar | 600/424 |
| 7,887,482 B2 | 2/2011 | Hamada | |
| 8,027,714 B2* | 9/2011 | Shachar | 600/424 |
| 8,128,644 B2 | 3/2012 | Carley et al. | |
| 8,150,499 B2 | 4/2012 | Gelbart et al. | |
| 8,337,524 B2 | 12/2012 | Gelbart et al. | |
| 8,449,605 B2 | 5/2013 | Lichtenstein et al. | |
| 8,532,746 B2 | 9/2013 | Gelbart et al. | |
| 8,672,998 B2 | 3/2014 | Lichtenstein et al. | |
| 2001/0003158 A1 | 6/2001 | Kensey et al. | 606/213 |
| 2001/0005787 A1 | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2001/0041915 A1 | 11/2001 | Roue et al. | |
| 2001/0044568 A1 | 11/2001 | Langberg et al. | 600/37 |
| 2002/0002329 A1 | 1/2002 | Avitall | |
| 2002/0013621 A1 | 1/2002 | Stobie et al. | |

(56) References Cited

U.S. PATENT DOCUMENTS

| | | | |
|---|---|---|---|
| 2002/0016628 A1 | 2/2002 | Langberg et al. | 623/2.36 |
| 2002/0026092 A1 | 2/2002 | Buckberg et al. | 600/37 |
| 2002/0055775 A1 | 5/2002 | Carpentier et al. | 623/2.17 |
| 2002/0082621 A1 | 6/2002 | Schurr et al. | |
| 2002/0087156 A1 | 7/2002 | Maguire et al. | |
| 2002/0087173 A1 | 7/2002 | Alferness et al. | 606/151 |
| 2002/0107478 A1 | 8/2002 | Wendlandt | |
| 2002/0107511 A1 | 8/2002 | Collins et al. | |
| 2002/0107530 A1 | 8/2002 | Sauer et al. | |
| 2002/0111647 A1* | 8/2002 | Khairkhahan et al. | 606/200 |
| 2002/0115944 A1 | 8/2002 | Mendes et al. | 600/594 |
| 2002/0133143 A1* | 9/2002 | Murphy | A61B 17/0218 606/1 |
| 2002/0161394 A1 | 10/2002 | Macoviak et al. | 606/200 |
| 2002/0161406 A1 | 10/2002 | Silvian | 607/5 |
| 2002/0169359 A1* | 11/2002 | McCarthy | A61B 17/00234 600/16 |
| 2002/0169360 A1 | 11/2002 | Taylor et al. | 600/37 |
| 2002/0169504 A1 | 11/2002 | Alferness et al. | 623/2.36 |
| 2002/0177782 A1 | 11/2002 | Penner | |
| 2002/0183836 A1 | 12/2002 | Liddicoat et al. | 623/2.11 |
| 2002/0183841 A1 | 12/2002 | Cohn et al. | 623/2.36 |
| 2002/0188170 A1 | 12/2002 | Santamore et al. | 600/37 |
| 2002/0198603 A1 | 12/2002 | Buckberg et al. | 623/23.71 |
| 2003/0018358 A1 | 1/2003 | Saadat | |
| 2003/0023241 A1 | 1/2003 | Drewry et al. | |
| 2003/0028202 A1 | 2/2003 | Sancoff et al. | |
| 2003/0032979 A1* | 2/2003 | Mortier | A61B 17/00234 606/213 |
| 2003/0036755 A1 | 2/2003 | Ginn | |
| 2003/0045896 A1 | 3/2003 | Murphy et al. | 606/191 |
| 2003/0050682 A1* | 3/2003 | Sharkey | A61B 17/12022 607/126 |
| 2003/0050685 A1* | 3/2003 | Nikolic et al. | 623/1.11 |
| 2003/0050693 A1 | 3/2003 | Quijano et al. | |
| 2003/0069570 A1 | 4/2003 | Witzel et al. | 606/28 |
| 2003/0069593 A1 | 4/2003 | Tremulis et al. | |
| 2003/0069636 A1 | 4/2003 | Solem et al. | 623/2.37 |
| 2003/0078465 A1 | 4/2003 | Pai et al. | 600/16 |
| 2003/0078652 A1 | 4/2003 | Sutherland | |
| 2003/0078671 A1* | 4/2003 | Lesniak | A61B 17/00234 623/23.64 |
| 2003/0083742 A1 | 5/2003 | Spence et al. | |
| 2003/0105384 A1* | 6/2003 | Sharkey et al. | 600/16 |
| 2003/0105520 A1 | 6/2003 | Alferness et al. | 623/2.36 |
| 2003/0109770 A1 | 6/2003 | Sharkey et al. | 600/16 |
| 2003/0124480 A1 | 7/2003 | Peacock | |
| 2003/0149333 A1 | 8/2003 | Alferness | 600/16 |
| 2003/0158570 A1* | 8/2003 | Ferrazzi | 606/191 |
| 2003/0163191 A1* | 8/2003 | Nikolic | A61B 17/12022 623/1.11 |
| 2003/0167055 A1 | 9/2003 | Kolata et al. | |
| 2003/0181819 A1 | 9/2003 | Desai | |
| 2003/0208210 A1 | 11/2003 | Dreyfuss et al. | |
| 2003/0212453 A1 | 11/2003 | Mathis et al. | |
| 2003/0220667 A1 | 11/2003 | van der Burg et al. | 606/200 |
| 2003/0229395 A1 | 12/2003 | Cox | 623/2.36 |
| 2004/0002626 A1* | 1/2004 | Feld | A61B 17/00234 600/37 |
| 2004/0054279 A1 | 3/2004 | Hanley | 600/424 |
| 2004/0064014 A1* | 4/2004 | Melvin | A61F 2/2487 600/37 |
| 2004/0122516 A1* | 6/2004 | Fogarty et al. | 623/2.37 |
| 2004/0127916 A1 | 7/2004 | Bolduc et al. | |
| 2004/0133220 A1 | 7/2004 | Lashinski et al. | |
| 2004/0133273 A1 | 7/2004 | Cox | 623/2.11 |
| 2004/0138529 A1 | 7/2004 | Wiltshire et al. | |
| 2004/0138744 A1 | 7/2004 | Lashinski et al. | 623/2.36 |
| 2004/0138745 A1 | 7/2004 | Macoviak et al. | |
| 2004/0153146 A1 | 8/2004 | Lashinski et al. | 623/2.36 |
| 2004/0153147 A1 | 8/2004 | Mathis | |
| 2004/0158321 A1 | 8/2004 | Reuter et al. | 623/2.36 |
| 2004/0176797 A1 | 9/2004 | Opolski | |
| 2004/0176800 A1 | 9/2004 | Paraschac et al. | |
| 2004/0186566 A1 | 9/2004 | Hindrichs et al. | 623/2.37 |
| 2004/0193187 A1 | 9/2004 | Boehringer et al. | |
| 2004/0215232 A1 | 10/2004 | Belhe et al. | 606/213 |
| 2004/0220593 A1 | 11/2004 | Greenhalgh | |
| 2004/0236419 A1 | 11/2004 | Milo | |
| 2004/0243170 A1* | 12/2004 | Suresh et al. | 606/198 |
| 2004/0249408 A1* | 12/2004 | Murphy | A61F 2/2487 606/198 |
| 2004/0249453 A1 | 12/2004 | Cartledge et al. | 623/2.37 |
| 2004/0260390 A1 | 12/2004 | Sarac et al. | |
| 2004/0260393 A1 | 12/2004 | Rahdert et al. | |
| 2004/0267191 A1 | 12/2004 | Gifford, III et al. | |
| 2004/0267358 A1 | 12/2004 | Reitan | 623/2.37 |
| 2005/0004668 A1* | 1/2005 | Aklog | A61F 2/2448 623/2.36 |
| 2005/0015109 A1* | 1/2005 | Lichtenstein | A61B 17/0057 606/200 |
| 2005/0038509 A1 | 2/2005 | Ashe | |
| 2005/0054938 A1 | 3/2005 | Wehman et al. | 600/483 |
| 2005/0055089 A1 | 3/2005 | Macoviak et al. | 623/2.37 |
| 2005/0060030 A1 | 3/2005 | Lashinski et al. | 623/2.37 |
| 2005/0064665 A1 | 3/2005 | Han | 438/286 |
| 2005/0065420 A1 | 3/2005 | Collins et al. | |
| 2005/0065504 A1 | 3/2005 | Melsky et al. | |
| 2005/0075727 A1 | 4/2005 | Wheatley | |
| 2005/0080402 A1 | 4/2005 | Santamore et al. | 606/1 |
| 2005/0090840 A1 | 4/2005 | Gerbino et al. | |
| 2005/0096047 A1 | 5/2005 | Haberman et al. | |
| 2005/0096498 A1* | 5/2005 | Houser et al. | 600/37 |
| 2005/0096589 A1* | 5/2005 | Shachar | 604/95.01 |
| 2005/0096647 A1 | 5/2005 | Steinke et al. | 606/41 |
| 2005/0107723 A1 | 5/2005 | Wehman et al. | 600/595 |
| 2005/0107871 A1 | 5/2005 | Realyvasquez et al. | 623/2.11 |
| 2005/0125030 A1 | 6/2005 | Forsberg et al. | 606/213 |
| 2005/0131441 A1 | 6/2005 | Iio et al. | |
| 2005/0137659 A1 | 6/2005 | Garabedian et al. | |
| 2005/0137689 A1 | 6/2005 | Salahieh et al. | |
| 2005/0137695 A1 | 6/2005 | Salahieh et al. | |
| 2005/0137700 A1 | 6/2005 | Spence et al. | 623/2.36 |
| 2005/0143809 A1 | 6/2005 | Salahieh et al. | |
| 2005/0148892 A1 | 7/2005 | Desai | |
| 2005/0149014 A1 | 7/2005 | Hauck et al. | 606/41 |
| 2005/0149114 A1 | 7/2005 | Cartledge et al. | |
| 2005/0154252 A1 | 7/2005 | Sharkey et al. | 600/37 |
| 2005/0177180 A1* | 8/2005 | Kaganov | A61B 17/00234 606/151 |
| 2005/0177227 A1 | 8/2005 | Heim et al. | |
| 2005/0182365 A1 | 8/2005 | Hennemann et al. | 604/113 |
| 2005/0187620 A1 | 8/2005 | Pai et al. | 623/2.37 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0197716 A1 | 9/2005 | Sharkey et al. | 623/23.67 |
| 2005/0203558 A1 | 9/2005 | Maschke | |
| 2005/0209636 A1 | 9/2005 | Widomski et al. | 606/213 |
| 2005/0216052 A1 | 9/2005 | Mazzocchi et al. | 606/200 |
| 2005/0216054 A1 | 9/2005 | Widomski et al. | 606/213 |
| 2005/0240249 A1 | 10/2005 | Tu et al. | 607/96 |
| 2005/0251116 A1 | 11/2005 | Steinke et al. | 606/8 |
| 2005/0251132 A1 | 11/2005 | Oral et al. | |
| 2005/0256521 A1 | 11/2005 | Kozel | |
| 2005/0267573 A9 | 12/2005 | Macoviak et al. | |
| 2005/0267574 A1 | 12/2005 | Cohn et al. | 623/2.36 |
| 2005/0273138 A1 | 12/2005 | To et al. | |
| 2006/0004424 A1 | 1/2006 | Loeb et al. | 607/63 |
| 2006/0009755 A1 | 1/2006 | Sra | |
| 2006/0009756 A1 | 1/2006 | Francischelli et al. | |
| 2006/0014998 A1 | 1/2006 | Sharkey et al. | 600/16 |
| 2006/0015002 A1 | 1/2006 | Moaddeb et al. | 600/37 |
| 2006/0015003 A1 | 1/2006 | Moaddes et al. | 600/37 |
| 2006/0015038 A1 | 1/2006 | Weymarn-Scharli | 600/585 |
| 2006/0015096 A1 | 1/2006 | Hauck et al. | |
| 2006/0025784 A1 | 2/2006 | Starksen et al. | |
| 2006/0025800 A1* | 2/2006 | Suresh | A61B 17/0057 606/198 |
| 2006/0030881 A1 | 2/2006 | Sharkey et al. | 606/213 |
| 2006/0052867 A1 | 3/2006 | Revuelta et al. | |
| 2006/0058871 A1 | 3/2006 | Zakay et al. | |
| 2006/0085049 A1 | 4/2006 | Cory et al. | |

(56) References Cited

U.S. PATENT DOCUMENTS

| | | | |
|---|---|---|---|
| 2006/0135968 A1 | 6/2006 | Schaller | 606/144 |
| 2006/0135970 A1 | 6/2006 | Schaller | 606/152 |
| 2006/0173536 A1 | 8/2006 | Mathis et al. | |
| 2006/0184242 A1 | 8/2006 | Lichtenstein | 623/2.37 |
| 2006/0199995 A1* | 9/2006 | Vijay | 600/37 |
| 2006/0229491 A1* | 10/2006 | Sharkey et al. | 600/37 |
| 2006/0235286 A1 | 10/2006 | Stone et al. | 600/381 |
| 2006/0235314 A1 | 10/2006 | Migliuolo et al. | |
| 2006/0241334 A1 | 10/2006 | Dubi et al. | 600/16 |
| 2006/0241745 A1 | 10/2006 | Solem | |
| 2006/0264980 A1* | 11/2006 | Khairkhahan | A61B 17/0057 606/153 |
| 2006/0276683 A1 | 12/2006 | Feld et al. | 600/16 |
| 2006/0281965 A1 | 12/2006 | Khairkhahan et al. | 600/37 |
| 2006/0293698 A1* | 12/2006 | Douk | A61B 17/08 606/142 |
| 2006/0293725 A1 | 12/2006 | Rubinsky et al. | |
| 2006/0293739 A1* | 12/2006 | Vijay | A61B 17/12022 607/122 |
| 2007/0010817 A1 | 1/2007 | de Coninck | |
| 2007/0016006 A1* | 1/2007 | Shachar | 600/424 |
| 2007/0016068 A1 | 1/2007 | Grunwald et al. | 600/468 |
| 2007/0016288 A1 | 1/2007 | Gurskis et al. | |
| 2007/0027533 A1 | 2/2007 | Douk | |
| 2007/0038208 A1 | 2/2007 | Kefer | |
| 2007/0050019 A1 | 3/2007 | Hyde | |
| 2007/0060895 A1* | 3/2007 | Sibbitt, Jr. | A61B 17/0057 604/215 |
| 2007/0083076 A1 | 4/2007 | Lichtenstein | 600/16 |
| 2007/0088362 A1 | 4/2007 | Bonutti et al. | |
| 2007/0115390 A1 | 5/2007 | Makara et al. | |
| 2007/0118151 A1* | 5/2007 | Davidson | A61B 17/00234 606/144 |
| 2007/0118215 A1 | 5/2007 | Moaddeb | 623/2.37 |
| 2007/0129717 A1 | 6/2007 | Brown, III et al. | |
| 2007/0135826 A1 | 6/2007 | Zaver et al. | |
| 2007/0135913 A1 | 6/2007 | Moaddeb et al. | |
| 2007/0156233 A1 | 7/2007 | Kapadia et al. | |
| 2007/0161846 A1* | 7/2007 | Nikolic | A61N 1/05 600/16 |
| 2007/0185571 A1 | 8/2007 | Kapadia et al. | |
| 2007/0198057 A1* | 8/2007 | Gelbart | A61B 17/0057 606/213 |
| 2007/0198058 A1* | 8/2007 | Gelbart | A61B 17/0057 606/213 |
| 2007/0213578 A1* | 9/2007 | Khairkhahan | A61B 17/0057 600/16 |
| 2007/0213815 A1 | 9/2007 | Khairkhanan et al. | 623/3.1 |
| 2007/0219460 A1 | 9/2007 | Goldenberg | |
| 2007/0225736 A1 | 9/2007 | Zeiner et al. | |
| 2007/0249999 A1 | 10/2007 | Sklar et al. | |
| 2007/0250160 A1 | 10/2007 | Rafiee | 623/2.11 |
| 2007/0270681 A1 | 11/2007 | Phillips et al. | |
| 2007/0270688 A1 | 11/2007 | Gelbart et al. | |
| 2007/0270943 A1 | 11/2007 | Solem et al. | |
| 2007/0299343 A1 | 12/2007 | Waters | |
| 2008/0004534 A1 | 1/2008 | Gelbart et al. | |
| 2008/0004643 A1 | 1/2008 | To et al. | 606/159 |
| 2008/0004697 A1 | 1/2008 | Lichtenstein et al. | 623/2.11 |
| 2008/0033541 A1 | 2/2008 | Gelbart et al. | |
| 2008/0045778 A1 | 2/2008 | Lichtenstein et al. | 600/16 |
| 2008/0051802 A1 | 2/2008 | Schostek et al. | |
| 2008/0071298 A1 | 3/2008 | Khairkhanan et al. | 606/151 |
| 2008/0086164 A1 | 4/2008 | Rowe | 606/191 |
| 2008/0132915 A1 | 6/2008 | Buckman et al. | |
| 2008/0133002 A1 | 6/2008 | Gelbart et al. | |
| 2008/0140188 A1 | 6/2008 | Rahdert et al. | |
| 2008/0177300 A1 | 7/2008 | Mas et al. | |
| 2008/0228266 A1 | 9/2008 | McNamara et al. | |
| 2008/0262609 A1 | 10/2008 | Gross et al. | |
| 2008/0269785 A1 | 10/2008 | Lampropoulos et al. | |
| 2008/0275477 A1 | 11/2008 | Sterrett et al. | |
| 2008/0288060 A1 | 11/2008 | Kaye et al. | |
| 2008/0312713 A1 | 12/2008 | Wilfley et al. | |
| 2009/0076597 A1 | 3/2009 | Dahlgren et al. | |
| 2009/0131930 A1 | 5/2009 | Gelbart et al. | |
| 2009/0157058 A1 | 6/2009 | Ferren et al. | |
| 2009/0192441 A1 | 7/2009 | Gelbart et al. | |
| 2009/0192527 A1 | 7/2009 | Messas | |
| 2009/0192539 A1 | 7/2009 | Lichtenstein | 606/191 |
| 2009/0204180 A1 | 8/2009 | Gelbart | |
| 2009/0287304 A1 | 11/2009 | Dahlgren et al. | 623/2.37 |
| 2010/0087836 A1 | 4/2010 | Jaramillo et al. | |
| 2010/0087837 A1 | 4/2010 | Jaramillo et al. | |
| 2010/0161047 A1 | 6/2010 | Cabiri | |
| 2010/0179648 A1 | 7/2010 | Richter et al. | |
| 2010/0222789 A1 | 9/2010 | Gelbart et al. | |
| 2011/0022166 A1 | 1/2011 | Dahlgren et al. | 623/2.11 |
| 2011/0082538 A1 | 4/2011 | Dahlgren et al. | |
| 2011/0087203 A1 | 4/2011 | Lichtenstein et al. | |
| 2011/0087227 A1 | 4/2011 | Mazur et al. | |
| 2011/0125172 A1 | 5/2011 | Gelbart et al. | |
| 2011/0172658 A1 | 7/2011 | Gelbart et al. | |
| 2011/0301618 A1 | 12/2011 | Lichtenstein | |
| 2012/0083806 A1 | 4/2012 | Goertzen | |
| 2012/0158016 A1 | 6/2012 | Gelbart et al. | |
| 2012/0245604 A1 | 9/2012 | Tegzes | |
| 2013/0041405 A1 | 2/2013 | Gelbart et al. | |
| 2013/0238089 A1 | 9/2013 | Lichtenstein et al. | |
| 2013/0345797 A1 | 12/2013 | Dahlgren et al. | |
| 2014/0135913 A1 | 5/2014 | Lichtenstein et al. | |
| 2015/0223802 A1 | 8/2015 | Tegzes | |

FOREIGN PATENT DOCUMENTS

| | | |
|---|---|---|
| WO | 90/15582 | 12/1990 |
| WO | 95/10320 A1 | 4/1995 |
| WO | 01/78625 | 10/2001 |
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/007031 A2 | 1/2005 |
| WO | 2005/046520 | 5/2005 |
| WO | 2005/070330 | 8/2005 |
| WO | 2005/102181 | 11/2005 |
| WO | WO 2005102181 A1 * | 11/2005 |
| WO | 2006/017809 | 2/2006 |
| WO | 2006/105121 A2 | 10/2006 |
| WO | 2006/135747 | 12/2006 |
| WO | 2006/135749 | 12/2006 |
| WO | 2007/021647 | 2/2007 |
| WO | 2007/115390 | 10/2007 |
| WO | 2008/002606 A2 | 1/2008 |
| WO | 2009/065042 A2 | 5/2009 |

OTHER PUBLICATIONS

Determination of Left Ventricular Preload and Afterload by Quantitative Echocardiography in Man Robert A. Ratshin, Charles E. Rackley and Richard O. Russell Circulation Research. 1974;34:711-718, originally published May 1, 1974 https://doi.org/10.1161/01.RES.34.5.711.*

Athanasuleas et al., "Surgical Anterior Ventricular Restoration for Ischemic Cardiomyopathy," *Operative Techniques in Thoracic and Cardiovascular Surgery* 7(2):66-75, May 2002.

Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.

Cardiac Implants, URL=http://nmtmedical.com/products/ci/index.htm, download date May 13, 2006, 1 page.

Cooley, "Ventricular Aneurysms and Akinesis," *Cleveland Clinic Quarterly* 45(1):130-132, 1978.

David et al., "Postinfarction Ventricular Septal Rupture: Repair by Endocardial Patch with Infarct Exclusion," *Journal of Thoracic and Card Surgery* 110(5):1315-1322, 1995.

Dor et al., "Late Hemodynamic Results After Left Ventricular Patch Repair Associated with Coronary Grafting in Patients with Postinfarc-

(56) References Cited

OTHER PUBLICATIONS tion Akinetic or Dyskinetic Aneurysm of the Left Ventricle," *Journal of Thoracic and Cardiovascular Surgery* 110(5):1291-1301, 1995.
Dor et al., "Left Ventricular Aneurysm: A New Surgical Approach," *Thoracic Cardiovascular Surgery* 37:11-19, 1989.
Dor, "Left Ventricular Aneurysms: The Endoventricular Circular Patch Plasty," *Seminars in Thoracic and Cardiovascular Surgery* 9(2):123-130, Apr. 1997.
European Search Report, dated Jun. 26, 2008, for EP 08100878, 11 pages.
International Preliminary Report on Patentability, dated Jan. 6, 2009, for PCT/US2007/014902, 8 pages.
Jatene, "Left Ventricular Aneurysmectomy," *Journal of Thoracic and Cardiovascular Surgery* 89(3):321-331, 1985.
Konings et al., "Development of an Intravascular Impedance Catheter for Detection of Fatty Lesions in Arteries," *IEEE Transactions on Medical Imaging*, 16(4):439-446, 1997.
Lichtenstein, "Method and Apparatus for Percutaneous Reduction of Anterior-Posterior Diameter of Mitral Valve," U.S. Appl. No. 10/690,131, filed Oct. 20, 2003, 31 pages.
Lichtenstein et al., "System for Improving Diastolic Dysfunction," Office Action dated Dec. 24, 2008 for U.S. Appl. No. 11/497,309, 8 pages.
Lichtenstein et al., "System for Improving Diastolic Dysfunction," Amendment filed Apr. 22, 2009 for U.S. Appl. No. 11/497,309, 23 pages.
Lichtenstein et al., "System for Improving Diastolic Dysfunction," Office Action dated Aug. 5, 2009 for U.S. Appl. No. 11/497,309, 10 pages.
Lichtenstein et al., "System for Improving Diastolic Dysfunction," Amendment filed Oct. 23, 2009 for U.S. Appl. No. 11/497,309, 9 pages.
Lichtenstein et al., "System for Improving Diastolic Dysfunction," Office Action dated Jan. 20, 2010 for U.S. Appl. No. 11/497,309, 10 pages.
Lichtenstein et al., "System for Improving Diastolic Dysfunction," Amendment filed Apr. 7, 2010 for U.S. Appl. No. 11/497,309, 8 pages.
Lichtenstein, "Methods and Devices for Altering Blood Flow Through the Left Ventricle," Office Action dated Mar. 26, 2007 for U.S. Appl. No. 10/622,129, 17 pages.
Lichtenstein, "Methods and Devices for Altering Blood Flow Through the Left Ventricle," Amendment dated Jul. 26, 2007 for U.S. Appl. No. 10/622,129, 17 pages.
Lichtenstein, "Methods and Devices for Altering Blood Flow Through the Left Ventricle," Office Action dated Nov. 14, 2007 for U.S. Appl. No. 10/622,129, 6 pages.
Lichtenstein, "Methods and Devices for Altering Blood Flow Through the Left Ventricle," Preliminary Amendment dated Feb. 14, 2008 for U.S. Appl. No. 10/622,129, 15 pages.
Lichtenstein, "Methods and Devices for Altering Blood Flow Through the Left Ventricle," Examiner's Amendment dated Mar. 2, 2009 for U.S. Appl. No. 10/622,129, 5 pages.
Lichtenstein, "Methods and Devices for Altering Blood Flow Through the Left Ventricle," Preliminary Amendment dated Mar. 6, 2006 for U.S. Appl. No. 10/571,165, 7 pages.
Lichtenstein, "Methods and Devices for Altering the Blood Flow Through the Left Ventricle," Office Action dated Jul. 9, 2010 for U.S. Appl. No. 10/571,165, 8 pages.
Mack, "New Techniques for Percutaneous Repair of the Mitral Valve," *Heart Failure Review*, 11:259-268, 2006.
Menicanti et al., "The Dor Procedure: What has Changed After Fifteen Years of Clinical Practice?" *Journal of Thoracic and Cardiovascular Surgery* 124(5):886-890, Nov. 2002.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.

Rivera et al., "Ventricular Aneurysms and Akinesis," *Cleveland Clinic Quarterly* 45(1):133-135, 1978.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.
Timek et al., "Septal-Lateral Annular Cinching Abolishes Acute Ischemic Mitral Regurgitation," *Journal of Thoracic and Cardiovascular Surgery*, 123(5):881-888, 2002.
Torrent-Guasp et al., "Spatial Orientation of the Ventricular Muscle Band and Approach to Partial Ventriculotomy in Heart Failure," *Pathogenesis and Treatment*, Ch. 36, pp. 685-693.
Valvano et al., "Thermal Conductivity and Diffusivity of Biomaterials Measured with Self-Heated Thermistors," *International Journal of Thermodynamics*, 6(3):301-311, 1985.
Written Opinion, dated Jun. 12, 2004, for PCT/IB2004/002581, 8 pages.
Gelbart et al., "Method and Device for Closing Holes in Tissue", Office Action dated Nov. 20, 2014 for U.S. Appl. No. 13/652,299, 9 pages.
Goertzen et al., "Tissue Anchor System", Notice of Allowance dated Dec. 3, 2014 for U.S. Appl. No. 13/247,380, 14 pgs.
Tegzes, "Medical Kit for Constricting Tissue or a Bodily Orifice, for Example, a Mitral Valve", Amendment filed Dec. 3, 2014 for U.S. Appl. No. 13/421,677, 17 pgs.
Dahlgren et al., "Medical Device, Kit and Method for Constricting Tissue or a Bodily Orifice, for Example, a Mitral Valve", Amendment filed Dec. 30, 2014 for U.S. Appl. No. 13/917,469, 18 pgs.
"Constellation Mapping Catheters", Brochure, Boston Scientific Corp., 2 pgs, © 2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Dahlgren et al., "Medical Device, Kit and Method for Constricting Tissue or a Bodily Orifice, For Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, For Example a Mitral Valve", Final Office Action dated Feb. 13, 2013 for U.S. Appl. No. 12/894,912, 35 pgs.
Dahlgren et al., "Medical Device, Kit and Method for Constricting Tissue or a Bodily Orifice, For Example a Mitral Valve", Office Action dated Aug. 30, 2012 for U.S. Appl. No. 12/894,912, 16 pgs.
Dahlgren et al., "Medical Device, Kit and Method for Constricting Tissue or a Bodily Orifice, For Example a Mitral Valve", Response filed Jun. 13, 2013 for U.S. Appl. No. 12/894,912, 3 pgs.
Dahlgren et al., "Medical Device, Kit and Method for Constricting Tissue or a Bodily Orifice, for Example, a Mitral Valve", Office Action dated Jul. 9, 2014 for U.S. Appl. No. 13/917,469, 37 pgs.
Goertzen et al., "Tissue Anchor System", Amendment filed Apr. 29, 2013 for U.S. Appl. No. 13/247,380, 22 pgs.
Goertzen et al., "Tissue Anchor System", Amendment filed Dec. 10, 2013 for U.S. Appl. No. 13/247,380, 11 pgs.
Goertzen et al., "Tissue Anchor System", Amendment filed Oct. 11, 2013 for U.S. Appl. No. 13/247,380, 10 pgs.
Goertzen et al., "Tissue Anchor System", Office Action dated Aug. 13, 2013 for U.S. Appl. No. 13/247,380, 15 pgs.
Goertzen et al., "Tissue Anchor System", Office Action dated Jan. 29, 2013 for U.S. Appl. No. 13/247,380, 10 pgs.
International Search Report dated Jun. 16, 2011 for PCT/US2010/050945, 5 pgs.

(56) References Cited

OTHER PUBLICATIONS

Lichtenstein "Closing Openings in Anatomical Tissue", Amendment filed Aug. 8, 2013 for U.S. Appl. No. 13/112,695, 23 pgs.
Lichtenstein "Closing Openings in Anatomical Tissue", Office Action dated May 8, 2013 for U.S. Appl. No. 13/112,695, 12 pgs.
Lichtenstein, "Closing Openings in Anatomical Tissue", Final Office Action dated Dec. 4, 2013 for U.S. Appl. No. 13/112,695, 31 pages.
Mazur et al., "Bone Fixation Device, Tools and Methods", U.S. Appl. No. 61/138,920, filed Dec. 18, 2008, 88 pgs.
STAR Closure System Brochure, 2005, Abbott Vascular, pp. 1-4.
Tegzes, "Medical Kit for Constricting Tissue or a Bodily Orifice, for Example, a Mitral Valve", Office Action dated Jul. 11, 2014 for U.S. Appl. No. 13/421,677, 9 pgs.
Becker, et al., "Ablation of Atrial Fibrillation: Energy Sources and Navigation Tools: A Review", Journal of Electrocardiology, vol. 37, Supplement 2004, pp. 55-62, 2004.
Calkins, Hugh, "Electrophysiology: Radiofrequency Catheter Ablation of Supraventricular Arrhythmias", Heart, 2001; 85; pp. 594-600.
Dahlgren et al, "Medical Device for Constricting Tissue or a Bodily Orifice, for Example a Mitral Valve", Office Action dated Sep. 13, 2012 for U.S. Appl. No. 12/899,407, 28 pgs.
Dahlgren et al., "Medical Device for Constricting Tissue or a Bodily Orifice, For Example a Mitral Valve", Amendment filed Apr. 13, 2010 for U.S. Appl. No. 12/120,195, 22 pgs.
Dahlgren et al., "Medical Device for Constricting Tissue or a Bodily Orifice, for Example a Mitral Valve", Amendment filed Aug. 8, 2013 for U.S. Appl. No. 12/899,407, 65 pages.
Dahlgren et al., "Medical Device for Constricting Tissue or a Bodily Orifice, for Example a Mitral Valve", Amendment filed Dec. 13, 2012 for U.S. Appl. No. 12/899,407, 22 pages.
Dahlgren et al., "Medical Device for Constricting Tissue or a Bodily Orifice, For Example a Mitral Valve", Office Action dated Dec. 18, 2009 for U.S. Appl. No. 12/120,195, 9 pgs.
Dahlgren et al., "Medical Device for Constricting Tissue or a Bodily Orifice, For Example a Mitral Valve", Office Action dated Jul. 7, 2010 for U.S. Appl. No. 12/120,195, 14 pgs.
Dahlgren et al., "Medical Device for Constricting Tissue or a Bodily Orifice, for Example a Mitral Valve", Office Action dated Mar. 8, 2013 for U.S. Appl. No. 12/899,407, 23 pages.
Dahlgren et al., "Medical Device for Constricting Tissue or a Bodily Orifice, For Example a Mitral Valve", Preliminary Amendment filed Oct. 6, 2010 in U.S. Appl. No. 12/899,407, 8 pgs.
Dahlgren et al., "Medical Device, Kit and Method for Constricting Tissue or a Bodily Orifice, For Example a Mitral Valve", U.S. Appl. No. 61/278,232, filed Oct. 1, 2009, 215 pgs.
Dahlgren et al., "System for Mechanical Adjustment of Medical Implants", Amendment filed Apr. 2, 2010 for U.S. Appl. No. 11/902,099, 19 pgs.
Dahlgren et al., "System for Mechanical Adjustment of Medical Implants", Amendment filed Nov. 1, 2010 for U.S. Appl. No. 11/902,099, 12 pgs.
Dahlgren et al., "System for Mechanical Adjustment of Medical Implants", Office Action dated Jul. 8, 2010 for U.S. Appl. No. 11/902,099, 37 pgs.
Dahlgren et al., "System for Mechanical Adjustment of Medical Implants", Office Action dated Oct. 5, 2009 for U.S. Appl. No. 11/902,099, 13 pgs.
De Ponti, et al., "Non-Fluoroscopic Mapping Systems for Electrophysiology: the Tool or Toy Dilemma After 10 Years", European Heart Journal, 2006; 27, pp. 1134-1136.
Gabriel, et al., "The Dielectric Properties of Biological Tissues: I. Literature Survey", Phys. Med. Biol.; 41, 1996, pp. 2231-2249.
Gelbart et al., "Artificial Valve", Amendment filed Jan. 29, 2010 for U.S. Appl. No. 11/497,306, 22 pgs.
Gelbart et al., "Artificial Valve", Office Action dated May 7, 2010 for U.S. Appl. No. 11/497,306, 12 pgs.
Gelbart et al., "Automatic Atherectomy System", Amendment filed Oct. 25, 2010 for U.S. Appl. No. 11/436,584, 9 pgs.
Gelbart et al., "Automatic Atherectomy System", Amendment filed Mar. 30, 2010 U.S. Appl. No. 11/436,584, 20 pgs.
Gelbart et al., "Automatic Atherectomy System", Amendment filed Aug. 4, 2009 for U.S. Appl. No. 11/436,584, 35 pgs.
Gelbart et al., "Automatic Atherectomy System", Amendment filed Sep. 15, 2011 U.S. Appl. No. 12/950,871, 21 pgs.
Gelbart et al., "Automatic Atherectomy System", Office Action dated Dec. 1, 2009 for U.S. Appl. No. 11/436,584, 8 pgs.
Gelbart et al., "Automatic Atherectomy System", Office Action dated Dec. 14, 2010 for U.S. Appl. No. 11/436,584, 12 pgs.
Gelbart et al., "Automatic Atherectomy System", Office Action dated Mar. 4, 2009 for U.S. Appl. No. 11/436,584, 6 pgs.
Gelbart et al., "Automatic Atherectomy System", Office Action dated Jun. 15, 2011 for U.S. Appl. No. 12/950,871, 16 pgs.
Gelbart et al., "Automatic Atherectomy System", Office Action dated Sep. 25, 2012 for U.S. Appl. No. 13/404,834, 24 pgs.
Gelbart et al., "Intra-Cardiac Mapping and Ablation Method", Amendment filed Feb. 23, 2011 for U.S. Appl. No. 11/475,950, 28 pgs.
Dahlgren et al., "Medical Device, Kit and Method for Constricting Tissue or a Bodily Orifice, for Example, a Mitral Valve", Office Action dated Mar. 5, 2015 for U.S. Appl. No. 13/917,469, 52 pgs.
Gelbart et al., "Method and Device for Closing Holes in Tissue", Amendment filed Feb. 5, 2015 for U.S. Appl. No. 13/652,299, 11 pages.
Gelbart et al., "Intra-Cardiac Mapping and Ablation Method", Amendment filed Mar. 5, 2008 for U.S. Appl. No. 11/475,950, 11 pgs.
Gelbart et al., "Intra-Cardiac Mapping and Ablation Method", Amendment filed Aug. 16, 2010 for U.S. Appl. No. 11/475,950, 22 pgs.
Gelbart et al., "Intra-Cardiac Mapping and Ablation Method", Office Action dated Nov. 23, 2010 for U.S. Appl. No. 11/475,950, 25 pgs.
Gelbart et al., "Intra-Cardiac Mapping and Ablation Method", Office Action dated Jun. 23, 2010 for U.S. Appl. No. 11/475,950, 18 pgs.
Gelbart et al., "Intra-Cardiac Mapping and Ablation Method", Pre Amend filed Aug. 29, 2007 for U.S. Appl. No. 11/475,950, 42 pgs.
Gelbart et al., "Liposuction System", Amendment filed Dec. 7, 2011 for U.S. Appl. No. 12/010,458, 15 pgs.
Gelbart et al., "Liposuction System", Amendment filed Jun. 10, 2011 for U.S. Appl. No. 12/010,458, 10 pgs.
Gelbart et al., "Liposuction System", Office Action dated Mar. 16, 2011 for U.S. Appl. No. 12/010,458, 12 pgs.
Gelbart et al., "Liposuction System", Office Action dated Sep. 14, 2011 for U.S. Appl. No. 12/010,458, 9 pgs.
Gelbart et al., "Medical Device for Use in Bodily Lumens, for Example an Atrium", Office Action dated Jul. 25, 2011 for U.S. Appl. No. 11/941,819, 9 pgs.
Gelbart et al., "Method and Device for Closing Holes in Tissue", Amendment filed Jan. 30, 2009 for U.S. Appl. No. 11/436,585, 5 pgs.
Gelbart et al., "Method and Device for Closing Holes in Tissue", Amendment filed Jun. 2, 2009 for U.S. Appl. No. 11/436,585, 7 pgs.
Gelbart et al., "Method and Device for Closing Holes in Tissue", Amendment filed May 4, 2012 for U.S. Appl. No. 12/777,883, 12 pgs.
Gelbart et al., "Method and Device for Closing Holes in Tissue", Amendment filed Oct. 26, 2009 for U.S. Appl. No. 11/436,585, 13 pgs.
Gelbart et al., "Method and Device for Closing Holes in Tissue", Amendment filed Sep. 22, 2008 for U.S. Appl. No. 11/436,585, 3 pgs.
Gelbart et al., "Method and Device for Closing Holes in Tissue", Office Action dated Feb. 23, 2012 for U.S. Appl. No. 12/777,883, 23 pgs.
Gelbart et al., "Method and Device for Closing Holes in Tissue", Office Action dated Jan. 2, 2009 for U.S. Appl. No. US 11/436,585, 11 pgs.
Gelbart et al., "Method and Device for Closing Holes in Tissue", Office Action dated Jul. 7, 2009 for U.S. Appl. No. 11/436,585, 9 pgs.

(56) References Cited

OTHER PUBLICATIONS

Gelbart et al., "Method and Device for Closing Holes in Tissue", Office Action dated Sep. 4, 2008 for U.S. Appl. No. 11/436,585, 8 pgs.
Gelbart, "System for Implanting a Microstimulator", Amendment filed Jan. 20, 2010 for U.S. Appl. No. 12/068,878, 26 pgs.
Gelbart, "System for Implanting a Microstimulator", Office Action dated Aug. 18, 2010 for U.S. Appl. No. 12/068,878, 11 pgs.
Gelbart, "System for Implanting a Microstimulator", Office Action dated Aug. 20, 2009 for U.S. Appl. No. 12/068,878, 12 pgs.
International Search Report dated Dec. 6, 2004 for PCT/IB2004/002581, 3 pgs.
International Search Report dated Jan. 8, 2007 for PCT/CA2006/001123, 5 pgs.
International Search Report dated Sep. 10, 2010 for PCT/US2010/021835, 4 pgs.
International Search Report datdd Sep. 4, 2009 for PCT/US2009/043612, 7 pgs.
International Search Report, dated Dec. 2, 2009 for PCT/US2008/083644, 4 pages.
International Search Report, dated Dec. 5, 2007 for PCT/US2007/014902, 4 pages.
Jaramillo et al, "Surgical Instrument and Method for Tensioning and Securing a Flexible Suture", Amendment filed Dec. 4, 2012 for U.S. Appl. No. 12/436,926, 19 pgs.
Jaramillo et al, "Surgical Instrument and Method for Tensioning and Securing a Flexible Suture", Amendment filed Feb. 27, 2012 for U.S. Appl. No. 12/436,926, 25 pgs.
Jaramillo et al, "Surgical Instrument and Method for Tensioning and Securing a Flexible Suture", Amendment filed Jul. 26, 2011 for U.S. Appl. No. 12/246,614, 41 pgs.
Jaramillo et al, "Surgical Instrument and Method for Tensioning and Securing a Flexible Suture", Amendment filed Mar. 14, 2011 for U.S. Appl. No. 12/246,614, 22 pgs.
Jaramillo et al, "Surgical Instrument and Method for Tensioning and Securing a Flexible Suture", Amendment filed Oct. 5, 2011 for U.S. Appl. No. 12/436,926, 32 pgs.
Jaramillo et al, "Surgical Instrument and Method for Tensioning and Securing a Flexible Suture", Office Action dated Dec. 13, 2010 for U.S. Appl. No. 12/246,614, 15 pgs.
Jaramillo et al, "Surgical Instrument and Method for Tensioning and Securing a Flexible Suture", Office Action dated Jan. 11, 2012 for U.S. Appl. No. 12/436,926, 26 pgs.
Jaramillo et al, "Surgical Instrument and Method for Tensioning and Securing a Flexible Suture", Office Action dated Jul. 8, 2011 for U.S. Appl. No. 12/436,926, 17 pgs.
Jaramillo et al, "Surgical Instrument and Method for Tensioning and Securing a Flexible Suture", Office Action dated May 27, 2011 for U.S. Appl. No. 12/246,614, 24 pgs.
Jaramillo et al, "Surgical Instrument and Method for Tensioning and Securing a Flexible Suture", Office Action dated Sep. 21, 2012 for U.S. Appl. No. 12/436,926, 14 pgs.
Lichtenstein "Method and Apparatus for Percutaneous Reduction of Anterior-Posterior Diameter of Mitral Valve", Office Action dated Dec. 1, 2008 for U.S. Appl. No. 11/400,260, 10 pgs.
Lichtenstein "Method and Apparatus for Percutaneous Reduction of Anterior-Posterior Diameter of Mitral Valve", Office Action dated May 15, 2006 for U.S. Appl. No. 10/690,131, 9 pgs.
Lichtenstein et al., "Method for Anchoring a Mitral Valve", Amendment filed Aug. 31, 2009 for U.S. Appl. No. 11/475,978, 24 pgs.
Lichtenstein et al., "Method for Anchoring a Mitral Valve", Amendment filed Mar. 26, 2010 for U.S. Appl. No. 11/475,978, 26 pgs.
Lichtenstein et al., "Method for Anchoring a Mitral Valve", Office Action dated Dec. 29, 2009 for U.S. Appl. No. 11/475,978, 7 pgs.
Lichtenstein et al., "Method for Anchoring a Mitral Valve", Office Action dated May 1, 2009 for U.S. Appl. No. 11/475,978, 6 pgs.
Lopes et al., "Enhanced Medical Device for Use in Bodily Cavities, for Example an Atrium", U.S. Appl. No. 61/435,213, filed Jan. 21, 2011, 320 pgs.
Lopes et al., "Enhanced Medical Device for Use in Bodily Cavities, for Example an Atrium", U.S. Appl. No. 61/485,987, filed May 13, 2011, 401 pgs.
Lopes et al., "Enhanced Medical Device for Use in Bodily Cavities, for Example an Atrium", U.S. Appl. No. 61/488,639, filed May 20, 2011, 434 pgs.
Lopes et al., "Enhanced Medical Device for Use in Bodily Cavities, for Example an Atrium", U.S. Appl. No. 61/515,141, filed Aug. 4, 2011, 508 pgs.
Tegzes, "Medical Kit for Constricting Tissue or a Bodily Orifice, for Example, a Mitral Valve", U.S. Appl. No. 61/467,883, filed Mar. 25, 2011, 167 pgs.
Written Opinion dated Jun. 16, 2011 for PCT/US2010/050945, 4 pgs.
Written Opinion dated Sep. 10, 2010 for PCT/US2010/021835, 6 pgs.
Written Opinion, dated Dec. 2, 2009, for PCT/US2008/083644, 9 pages.
Written Opinion, dated Dec. 5, 2007, for PCT/US2007/014902, 7 pages.
Written Opinion, dated Jan. 8, 2007 for PCT/CA2006/001123, 6 pgs.
Written Opinion, dated Sep. 4, 2009 for PCT/US2009/043612, 6 pgs.
Extended European Search Report dated Sep. 18, 2014 for EP 10821276.2, 10 pages.
Dahlgren et al., "Medical Device for Constricting Tissue or a Bodily Orifice, for Example a Mitral Valve", Amendment filed Jul. 23, 2013 for U.S. Appl. No. 12/899,407, 60 pages.
Gelbart et al., "Automatic Atherectomy System", Notice of Allowance dated May 10, 2013 and Certificate of Correction dated May 6, 2014 for U.S. Appl. No. 13/404,834, 11 pgs.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance dated Aug. 20, 2010 for U.S. Appl. No. 11/436,584, 12 pgs.
Gelbart et al., "Automatic Atherectomy System", Notice of Allowance dated Nov. 25, 2011 and Certificate of Correction dated Jul. 17, 2012 for U.S. Appl. No. 12/950,871, 24 pgs.
Gelbart et al., "Method and Device for Closing Holes in Tissue", Response to Quayle Action filed Jul. 14, 2014 for U.S. Appl. No. 13/652,299, 29 pages.
Gelbart et al., "Method and Device for Closing Holes in Tissue", Quayle Action dated May 20, 2014 for U.S. Appl. No. 13/652,299, 25 pages.
Gelbart et al., "Method and Device for Closing Holes in Tissue", Preliminary Amendment filed Feb. 21, 2013 for U.S. Appl. No. 13/652,299, 9 pages.
Gelbart et al., "Method and Device for Closing Holes in Tissue", Notice of Allowance dated Feb. 24, 2010, Supplemental Notice of Allowance dated Mar. 24, 2010 and Remarks filed after allowance dated Apr. 9, 2010 for U.S. Appl. No. 11/436,585, 20 pgs.
Gelbart et al., "Method and Device for Closing Holes in Tissue", Notice of Allowance dated Aug. 22, 2012 for U.S. Appl. No. 12/777,883, 12 pgs.
Goertzen et al., "Tissue Anchor System", Notice of Allowance dated Jul. 7, 2014 for U.S. Appl. No. 13/247,380, 8 pgs.
Goertzen et al., "Tissue Anchor System", Notice of Allowance dated Oct. 16, 2014 for U.S. Appl. No. 13/247,380, 41 pgs.
Lichtenstein et al., "Method for Anchoring a Mitral Valve", Notices of Allowance dated Oct. 2, 2013 and Nov. 13, 2013 for U.S. Appl. No. 13/872,870, 35 pgs.
Lichtenstein et al., "Method for Anchoring a Mitral Valve", Notice of Allowance dated Jan. 28, 2013 for U.S. Appl. No. 11/475,978, 24 pgs.
Lichtenstein et al., "Method for Anchoring a Mitral Valve", Preliminary Amendment filed Jan. 24, 2014 for U.S. Appl. No. 14/162,469, 9 pgs.
Lichtenstein et al., "System for Improving Diastolic Dysfunction", Notice of Allowance dated Jul. 12, 2010 for U.S. Appl. No. 11/497,309, 8 pgs.

(56) References Cited

OTHER PUBLICATIONS

Gelbart "Method and Device for Closing Holes in Tissue", Office Action dated May 14, 2015 for U.S. Appl. No. 13/652,299, 67 pages.
Dahlgren et al., "Medical Device, Kit and Method for Constricting Tissue or a Bodily Orifice, for Example, a Mitral Valve", Amendment filed Jun. 4, 2015 for U.S. Appl. No. 13/917,469, 17 pgs.
Lichtenstein et al., "Method for Anchoring a Mitral Valve", Amendment filed Jun. 30, 2015 for U.S. Appl. No. 14/162,469, 7 pages.
Lichtenstein et al., "Method for Anchoring a Mitral Valve", Office Action dated Apr. 24, 2015 for U.S. Appl. No. 14/162,469, 61 pages.
Gelbart et al., "Method and Device for Closing Holes in Tissue", Amendment filed Aug. 14, 2015 for U.S. Appl. No. 13/652,299, 16 pages.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Amendment filed in co-pending U.S. Appl. No. 12/899,407 dated Jan. 20, 2017.
Office Action issued in co-pending U.S. Appl. No. 14/955,544 dated Mar. 21, 2017.
Amendment filed in U.S. Appl. No. 12/899,407 dated Jun. 14, 2016.
Office Action issued in U.S. Appl. No. 12/899,407 dated Sep. 1, 2016.
Office Action issued in U.S. Appl. No. 12/899,407 dated Dec. 23, 2015.
Office Action issued in U.S. Appl. No. 13/652,299 dated Nov. 4, 2015.
Notice of Allowance issued in U.S. Appl. No. 13/652,299 dated Oct. 28, 2016.
Amendment filed in U.S. Appl. No. 13/652,299 dated Sep. 30, 2016.
Notice of Allowance issued in copending U.S. Appl. No. 12/899,407 dated May 5, 2017.
Intention to Grant issued in European Patent Application No. 10821276.2 dated Jan. 3, 2017.
Intention to Grant issued in European Patent Application No. 10821276.2 dated May 9, 2017.
Amendment filed in copending U.S. Appl. No. 12/899,407 dated May 25, 2017.
Amendment filed in copending U.S. Appl. No. 14/955,544 dated Jun. 30, 2017.
Notice of Allowance issued in copending U.S. Appl. No. 14/955,544 dated Sep. 5, 2017.
Office Action issued in copending U.S. Appl. No. 14/696,853 dated Sep. 26, 2017.

* cited by examiner

SYSTEM FOR IMPROVING DIASTOLIC DYSFUNCTION

CROSS REFERENCE TO RELATED APPLICATIONS

This application is a continuation of U.S. patent application Ser. No. 11/497,309, now allowed, which has a filing date of Aug. 2, 2006 which is incorporated herein by reference in its entirety.

FIELD OF THE INVENTION

This application relates to cardiac surgery, and in particular to methods of treating heart failure such as congestive heart failure and diastolic dysfunction by percutaneous surgery.

BACKGROUND OF THE INVENTION

Diastolic dysfunction (i.e., insufficient expansion of the left ventricle during the diastolic phase) and general deterioration of the left ventricular performance are very common problems, affecting about 5 million people in the US alone. The problems can be triggered by a myocardial infraction or develop slowly over time. More background data on congestive heart failure can be found on the internet at: http://healthlink.mcw.edu/article/928348606.html and many other medical sources.

Prior art treatment can be classified generally into three methods: surgery to change the shape of the left ventricle, wrapping the heart in an elastic net, or introducing a reinforcing structures via a catheter into the left ventricle. The first two methods require extensive surgery. The prior art minimally invasive or percutaneous procedures such as disclosed by US patent applications 2005/0015109; 2004/0243170; 2004/0249408 and 2006/0025800 addressed the need of strengthening the heart wall to resist remodeling and enlargement due to systolic pressure, but do not improve diastolic expansion to allow better filling of the left ventricle with blood. In many cases prior art methods actually sacrifice diastolic function in exchange for preventing the abnormal enlargement of the left ventricle that often follows myocardial infraction. For example, wrapping the heart in an elastic net will assist systolic action and will limit left ventricle enlargement, but will interfere with diastolic function as it will require more force to expand the left ventricle and stretch the net. The same is true for any rigid internal reinforcement.

SUMMARY OF THE INVENTION

As taught herein a system may assist diastolic function, the system being able to fit through a catheter and be installed percutaneously. The system may also limit the enlargement of the left ventricle, thus solving two major problem of congestive heart failure in a single percutaneous procedure. Further advantages will become clear by studying the disclosure and the drawings.

An elastic structure is introduced percutaneously into the left ventricle and attached to the walls of the ventricle. Over time the structure bonds firmly to the walls via scar tissue formation. The structure helps the ventricle expand and fill with blood during the diastolic period while having little affect on systolic performance. The structure also strengthens the ventricular walls and limits the effects of congestive heart failure, as the maximum expansion of the support structure is limited by flexible or elastic members.

BRIEF DESCRIPTION OF THE DRAWINGS

FIG. 2-B is a cross sectional view of the left ventricle of the heart after deployment of the device of FIG. 1 therein.

DETAILED DESCRIPTION OF THE INVENTION

Various embodiments of a cardiac device comprise an elastic structure that it introduced into a left ventricle of a heart and assists diastolic function by gently trying to expand the left ventricle. The elastic force is a small fraction of the force during systolic contraction, thus the device has little effect on the systolic pressure or ejected volume. It is well known that diastolic dysfunction is a major cause of cardiovascular failure, as it is far more common than systolic dysfunction. After some time (weeks to months) scar tissue permanently binds the elastic structure of the device to the ventricular wall. At this point the device also prevents ventricular enlargement, acting as reinforcement to the ventricular wall and limiting the maximum size of the left ventricle. Since the enlargement of the left ventricle as a result of congestive heart failure or infarct is gradual, scar tissue will have a chance to form before full bond strength is required between the elastic structure of the device and the ventricular wall.

Figure 1:
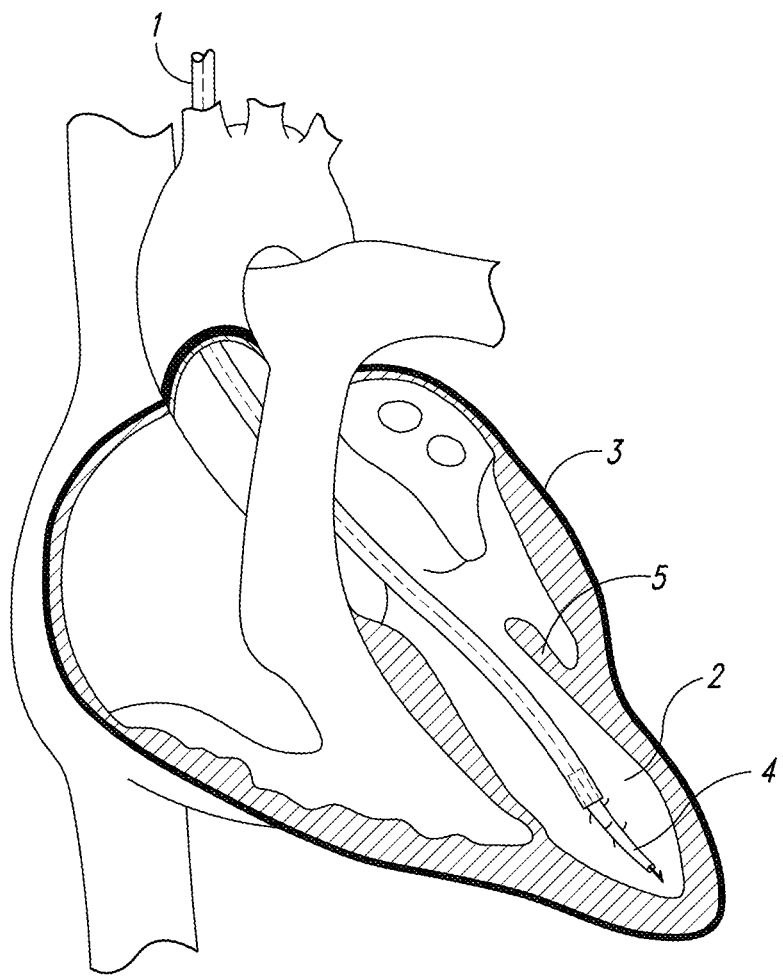
FIG. 1 is a cross sectional view of a heart showing an embodiment a cardiac device deployed in a left ventricle of the heart.

FIG. 1 shows a typical deployment of a cardiac device 4 according to one illustrated embodiment of the invention. Deployment is performed via a catheter 1 inserted through the aorta into a left ventricle 2 of a heart 3. Any method of accessing the left ventricle can be used, such as trans-septal or via the apex of the left ventricle. The catheter size is in the same range as other percutaneous cardiac procedures, using sizes in the range of 18 Fr to 28 Fr (about 6 to 9 mm). The cross section also shows the papillary muscles 5 and device 4.

FIG. 2-A shows the device 4 still inside catheter 1. Device 4 is held by flexible cable 7 which is used to push the device 4 through the catheter 1, typically via a hemostatic seal outside the body (not shown). Typically a guide wire 11 is used to guide the catheter 1 into the left ventricle 2.

Figures 2A, 2B:
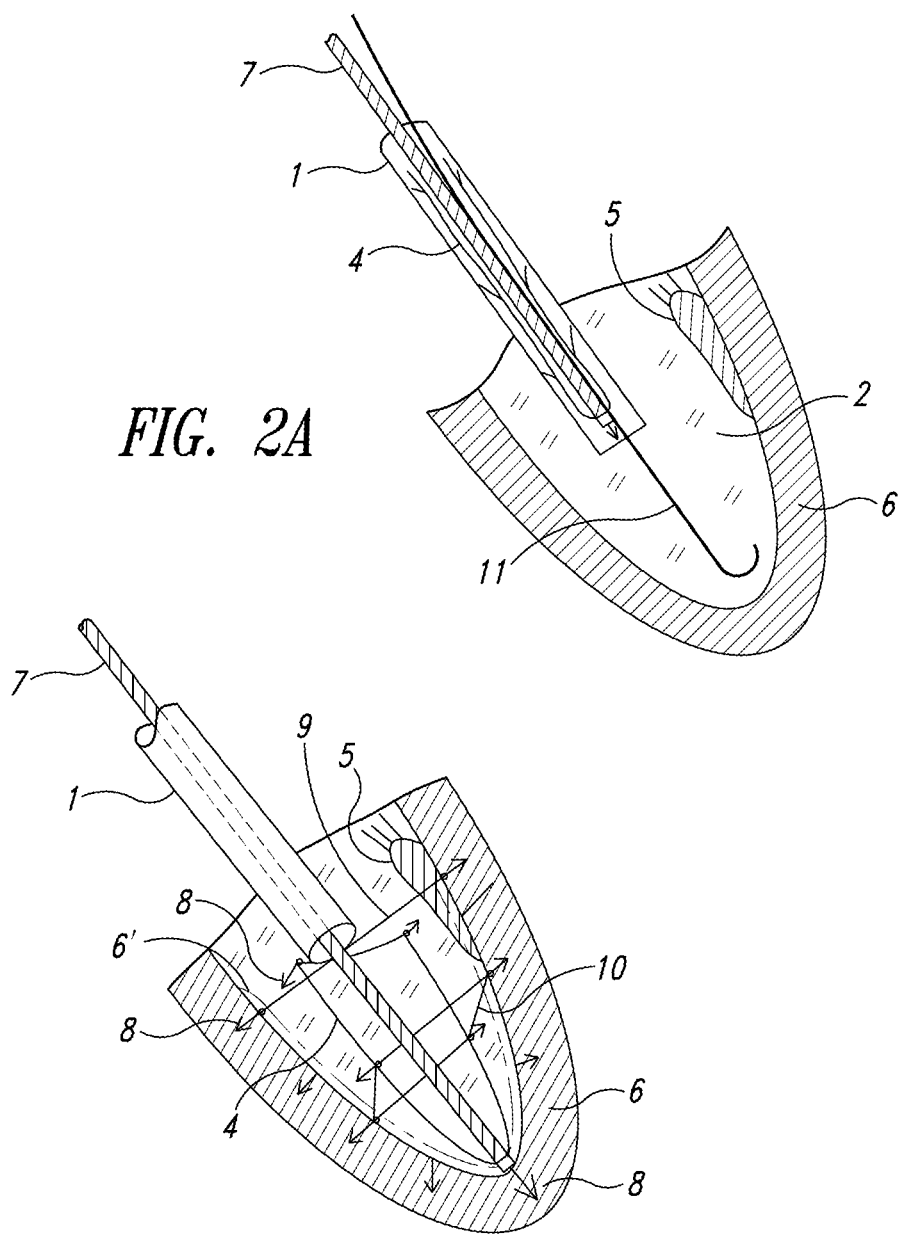
FIG. 2-A is a cross sectional view of the left ventricle of the heart with the device of FIG. 1 still in a catheter.

FIG. 2-B shows the device 4 after deployment in the left ventricle 2 of a heart 3. The device 4 expands elastically to fill the left ventricle 2. Ventricular contractions help embed a number of barbs 8 into a ventricular wall 6. Over time, scar tissue 6' forms a permanent bond between the device 4 and the ventricular wall 6. The maximum opening of the device 4 is limited not only by the ventricular wall 6 but by flexible cross-members 9 and 10. It is desired to connect members 9 across the device 4 rather than between adjacent arms (as shown by reference numeral 10) as this allows the cross member to clear the papillary muscles, allowing the device 4 to cover a larger part o the left ventricle 2. As seen in FIG. 2B, the papillary muscles 5 can fit between two elastic members of device 4.

Figure 3:
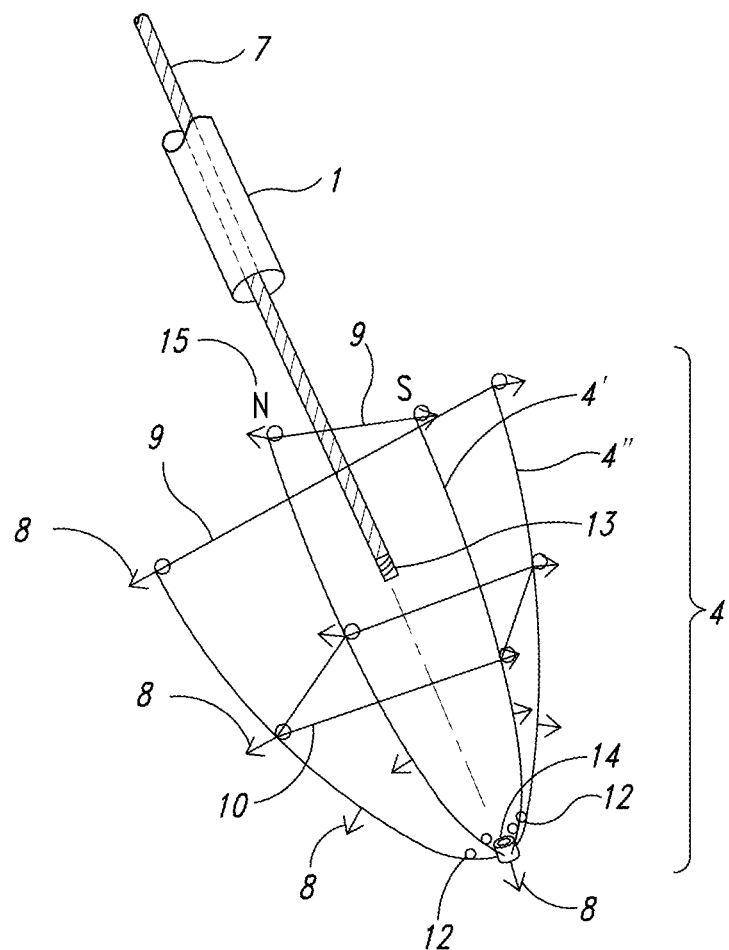
FIG. 3 is a perspective view of an embodiment of the invention.

FIG. 3 provides a more detailed view of the device of FIGS. 1, 2-A and 2-B. The cardiac device 4 has two pairs of elastic arms 4' and 4". The arms 4' and 4" are equipped with barbs 8 and cross members 9 and 10. The arms 4' and 4" can be made from any durable elastic material such Nitinol, spring tempered stainless steel, plated beryllium copper or polymeric material. For added elasticity small loops 12 can be added. At an apex of the device 4 a connector 14, such as a thread, is used for temporary attachment to the flexible cable 7 via a thread 13. Cross members 9 and 10 can be flexible steel cables, polymeric cables, flexible ribbons or similar flexible members. The purpose of members 9 and 10 is to limit the maximum dilation of the ventricle 2 and stop ventricular enlargement (after members 4' and 4" bond to ventricle wall 6 by scar tissue 6').

The number of flexible members 4' and 4" of device 4 and number of cross members 9, 10 can vary, the preferred embodiment having from three to twelve elastic members 9, 10. Cross members 9, 10 can connect adjacent elastic members 4' and 4" as members 10 do, or connect opposing members 4' and 4" as members 9 do. The arrangement shown in FIG. 3 is desired in order to allow elastic members 4' and 4" to extend beyond the papillary muscles 5 without cross members 9 touching the papillary muscles 5 or mitral valve cords (also known as chordae tendineae). Like any spring, the force that elastic members 4' and 4" exert on ventricle wall 6 is $F=k(x+a)$, "k" being the spring constant, "a" the preload (amount of spring preload beyond the fully dilated position) and "x" the ventricular wall movement. The spring constant k is selected not to interfere with systolic function while still helping diastolic filling. By the way of example, a total force the ventricular wall 6 is capable of exerting on each one of the elastic members 4' and 4" is about 20-30 Nt (about 2-3 Kg) and the average movement during contraction is about 1-2 cm. In order to limit the effect on systolic operation the total force is chosen to be below 10% of systolic force, or about 2 Nt. If a preload of 2 cm is chosen, the spring constant can be calculated from the equation: $2\ Nt=k(0.02\ m+0.02\ m)$, $k=50\ Nt/m$. The size (i.e., diameter) of wire forming elastic members 4' and 4" is determined by the spring constant k. The size is typically in the range of 0.5-1 mm.

In order to place the device 4 correctly relative to the papillary muscles 5 the orientation of the device 4 inside the left ventricle 6 needs to be known. This can be done by fluoroscopy, ultrasound or by other location methods such as magnetizing elastic members 4' but not 4". This creates a north and south pole 15 which can be detected from outside the body by a magnetometer (or even a very sensitive magnetic compass).

Figure 4:
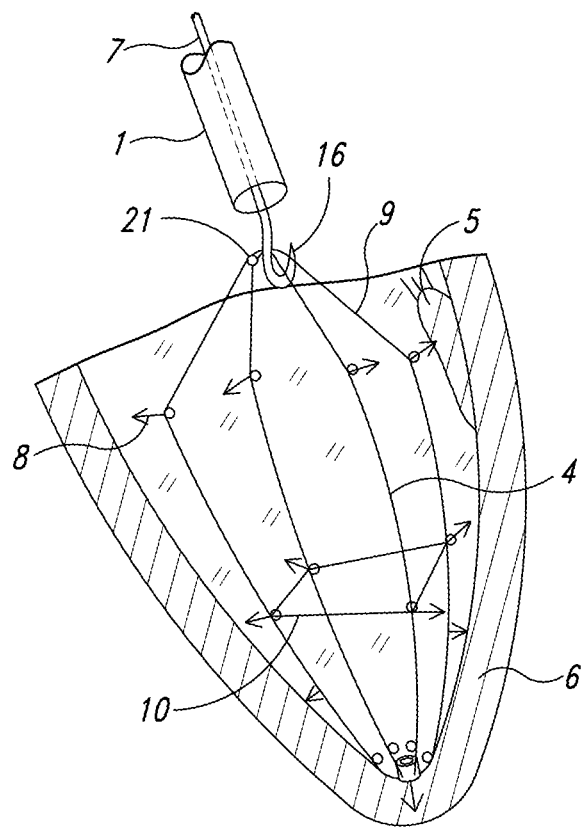
FIG. 4 is a cross sectional view of a left ventricle of a heart showing a device being retrieved therefrom using a catheter.
Figure 5A:
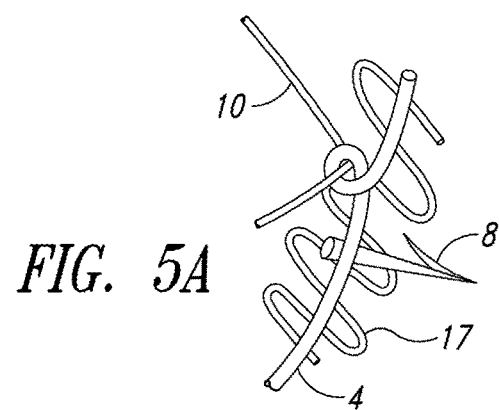
FIGS. 5-A, 5-B, 5-C and 5-D show different embodiments of the cardiac device, according to further illustrated embodiments.
Figure 5B:
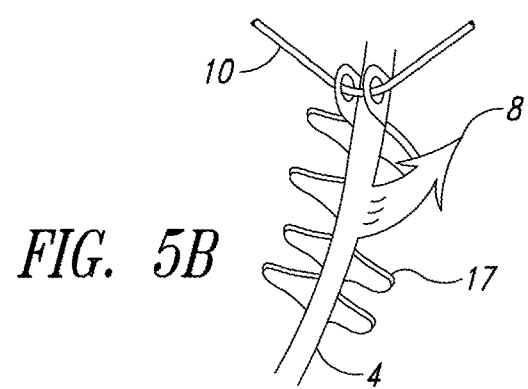
Figure 5C:
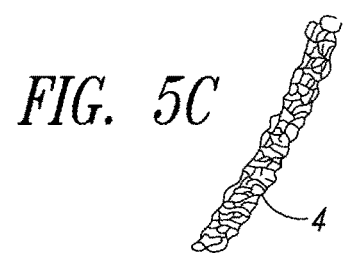
Figure 5D:
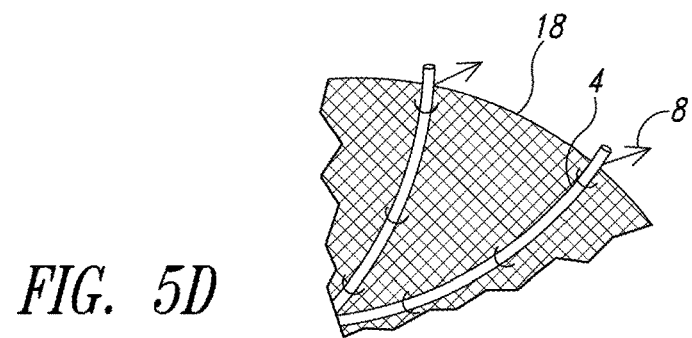

The design of the device 4 allows aborting the deployment at any stage and retrieving the device 4. This is illustrated in FIG. 4. A flexible cable 7 terminating in a hook 16 is introduced via a catheter 1.

Cross members 9 are snagged by the hook 16 and the device 4 is pulled back into the catheter 1. If retrieval is desirable the two cross members 9 should be permanently joined at a cross-over point 21. This allows the hook 16 to self-center regardless of the point at which the hook 16 snagged cross members 9 and regardless whether the hook 16 has snagged one or both cross members 9. Obviously the retrieval is much more difficult once scar tissue 6' has developed.

FIGS. 5-A through 5-D offer a more detailed close-up view of the construction of the device 4. FIG. 5-A shows the elastic elements 4' and 4" of the device 4 made of spring wire, cross members 10 made of thin stainless steel cable and barb 8 made of steel wire spot welded to the remainder of the device 4. If needed, a load spreading structure 17 can be added. The load spreading structure 17 can be made of bent wire, spot welded to remainder of the device 4 as shown, or can take the form of a polymeric strip. The complete device 4 can be coated with an anti-coagulant coating, drug eluting coating or any beneficial coating well known from the art of stents.

FIG. 5-B shows an alternate illustrated embodiment, cut out from a single sheet of elastic material and bent to shape. This mode of construction particularly advantageous when device 4 is made of Nitinol, as Nitinol is difficult to join. As before, an optional load spreading structure 17 can be added.

FIG. 5-C shows an embodiment of a device 4 that does not use discrete barbs but providing elastic members 4 with a special surface finish to promote rapid bonding with ventricular wall 6. Some examples of such finishes are: porous surfaces, surfaces coated with biological adhesives, surfaces coated with miniature barbs similar to the well known Velcro® fastener (generically termed hook and loop fastener), growth-promoting drug coating etc. It is known in the art that velour-like finishes promote tissue infiltration and greatly increase bonding strength. Test results are listed in U.S. Pat. No. 4,164,046 hereby incorporated by reference.

FIG. 5-D shows an embodiment in which the cross members are replaced with a continuous layer of a flexible mesh or flexible hemostatic material 18, such as Dacron fabric. When the layer 18 is hemostatic the device 4 can also seal an aneurysm or puncture in the ventricular wall 6, while still providing the other stated benefits. This is particularly desirable when the ventricular wall 6 is already significantly thinned by enlargement.

While the examples shown use a catheter 1 to enter the left ventricle 6 via the mitral valve, it is obvious that various other techniques may be employed to deploy the device 4. The device 4 can be installed in the left ventricle 6 also via the aortic valve, by piercing an apex of the left ventricle 6 or by an incision at any convenient point. It can be used percutaneously or during conventional cardiac surgery.

What is claimed is:
1. A cardiac medical device, comprising:
a plurality of elastic arms physically coupled together, the plurality of elastic arms movable between a first configuration in which the cardiac medical device is sized to be inserted into a left ventricle of a heart and a second configuration in which the plurality of elastic arms are configured to physically engage portions of a wall that forms the left ventricle and exert expansion force to assist an expansion of the left ventricle during a diastolic phase of a cardiac cycle,
wherein a portion of at least one elastic arm of the plurality of elastic arms includes a respective 360 degree loop configured to increase elasticity of the at least one elastic arm and located at least proximate a location where the plurality of elastic arms are physically coupled together, the respective 360 degree loop protruding into an interior volume bounded by the plurality of elastic arms.
2. The cardiac medical device of claim 1, further comprising:
a coupling that allows the cardiac medical device to be retrieved from the left ventricle via a catheter.

3. The cardiac medical device of claim 1 wherein at least one elastic arm of the plurality of elastic arms includes a sharp barb receivable in the wall.

4. The cardiac medical device of claim 1 wherein at least two elastic arms of the plurality of elastic arms each includes load spreaders extending laterally therefrom.

5. The cardiac medical device of claim 1 wherein a portion of each elastic arm of at least one elastic arm of the plurality of elastic arms includes a respective loop formed between opposed ends of the elastic arm, the respective loop distinct from the respective 360 degree loop.

6. The cardiac medical device of claim 1, further comprising:
a connector that physically couples the plurality of elastic arms to one another, the connector comprising at least one thread that is selectively threadedly engageable and disengageable from a flexible cable configured to facilitate percutaneous delivery of the cardiac medical device via a catheter.

7. The cardiac medical device of claim 1, wherein
the plurality of elastic arms are arranged about an axis in a circumferential arrangement when the plurality of elastic arms are in the second configuration,
the cardiac medical device further comprises at least one flexible cross-member expansion limiter physically coupled at least to a pair of non-adjacent arms of the plurality of elastic arms to limit an expansion of at least the pair of non-adjacent arms, the pair of non-adjacent arms non-adjacent along the circumferential arrangement when the plurality of elastic arms are in the second configuration, and
at least portions of the at least one flexible cross-member expansion limiter are physically coupled to at least the pair of non-adjacent arms, at a respective location on each of at least the pair of non-adjacent arms that does not vary as the plurality of elastic arms moves between the first and the second configurations, the at least the portions of the at least one flexible cross-member expansion limiter physically coupled to at least the pair of non-adjacent arms while bypassing an adjacent arm adjacent a first arm of the pair of non-adjacent arms along the circumferential arrangement when the plurality of elastic arms are in the second configuration.

8. The cardiac medical device of claim 7 wherein the cardiac medical device is configured, at least in a state in which the cardiac medical device has been implanted in the left ventricle in the second configuration of the plurality of elastic arms, to cause each elastic arm of a set of at least some of the plurality of elastic arms to contact respective portions of the wall at locations spaced relatively above a point at which a set of papillary muscles extend from the wall, and to cause physical coupling positions between at least a portion of the at least one flexible cross-member expansion limiter and at least two elastic arms of the plurality of elastic arms to be relatively above the point at which the set of papillary muscles extend from the wall.

9. The cardiac medical device of claim 8 wherein the cardiac medical device is configured, at least in the state in which the cardiac medical device has been implanted in the left ventricle in the second configuration of the plurality of elastic arms, to cause the physical coupling positions between the at least the portion of the at least one flexible cross-member expansion limiter and the at least two elastic arms to be relatively above the point at which the set of papillary muscles extend from the wall without the at least the portion of the at least one flexible cross-member expansion limiter interfering with the set of papillary muscles or with a number of chordae tendineae.

10. The cardiac medical device of claim 7 wherein the plurality of elastic arms and the at least one flexible cross-member expansion limiter are configurable to be delivered by a catheter.

11. The cardiac medical device of claim 7 wherein the plurality of elastic arms, the at least one flexible cross-member expansion limiter, or both the plurality of elastic arms and the at least one flexible cross-member expansion limiter is or are made of a flexible metal wire material.

12. The cardiac medical device of claim 7 wherein the plurality of elastic arms, the at least one flexible cross-member expansion limiter, or both the plurality of elastic arms and the at least one flexible cross-member expansion limiter is or are made of a polymeric material.

13. The cardiac medical device of claim 7 wherein the plurality of elastic arms, the at least one flexible cross-member expansion limiter, or both the plurality of elastic arms and the at least one flexible cross-member expansion limiter comprises or comprise a biologically beneficial coating.

14. The cardiac medical device of claim 7 wherein the flexible cross-member expansion limiter is spaced relatively inwardly from distal ends of the plurality of elastic arms when the plurality of elastic arms are in the second configuration.

15. The cardiac medical device of claim 7 wherein
the portions of the at least one flexible cross-member expansion limiter include a first portion physically coupled to the first arm of the pair of non-adjacent arms at a first location,
the portions of the at least one flexible cross-member expansion limiter include a second portion physically coupled to a second arm of the pair of non-adjacent arms at a second location, and
the first arm of the pair of non-adjacent arms is free from any coupling to the adjacent arm at the first location.

16. The cardiac medical device of claim 7 wherein the portions of the at least one flexible cross-member expansion limiter are physically coupled to at least the pair of non-adjacent arms at a same respective location on each of at least the pair of non-adjacent arms when the plurality of elastic arms are in each of the first and the second configurations.

17. The cardiac medical device of claim 7 wherein the at least one flexible cross-member expansion limiter comprises a first elongated cross-member physically coupled to a first pair of non-adjacent arms of the plurality of elastic arms non-adjacent along the circumferential arrangement when the plurality of elastic arms are in the second configuration, and a second elongated cross-member physically coupled to a second pair of non-adjacent arms of the plurality of elastic arms non-adjacent along the circumferential arrangement when the plurality of elastic arms are in the second configuration, the second pair of non-adjacent arms different than the first pair of non-adjacent arms, the first elongated cross-member and the second elongated cross-member fixedly joined together at a cross-over point where the first and the second elongated cross-members cross each other.

18. The cardiac medical device of claim 7 wherein the at least one flexible cross-member expansion limiter comprises a first elongated cross-member physically coupled to a first pair of elastic arms of the plurality of elastic arms, the first pair of elastic arms adjacent one another along the circumferential arrangement when the plurality of elastic arms are in the second configuration.

19. The cardiac medical device of claim 18 wherein the at least one flexible cross-member expansion limiter comprises a second elongated cross-member physically coupled to a second pair of elastic arms of the plurality of elastic arms, the second pair of elastic arms different than the first pair of elastic arms, the second pair of elastic arms opposed to one another across the circumferential arrangement when the plurality of elastic arms are in the second configuration.

20. The cardiac medical device of claim 19 wherein the cardiac medical device is configured, at least in a state in which the cardiac medical device has been implanted in the left ventricle in the second configuration of the plurality of elastic arms, to cause each elastic arm of a first set of at least some of the plurality of elastic arms to contact respective portions of the wall at locations spaced relatively above a point at which a set of papillary muscles extend from the wall, and to cause the second elongated cross-member to be arranged with respect to the first elongated cross-member such that the point at which the set of papillary muscles extend from the wall is located between the first and the second elongated cross members.

21. The cardiac medical device of claim 7 wherein the cardiac medical device is configured, at least in a state in which the cardiac medical device has been implanted in the left ventricle in the second configuration of the plurality of elastic arms, to cause each elastic arm of the plurality of elastic arms to contact respective portions of the wall at locations spaced relatively above a point at which a set of papillary muscles extend from the wall, and to cause a physical coupling position or physical coupling positions between at least a first portion of the at least one flexible cross-member expansion limiter and a first set of at least some of the plurality of elastic arms to be relatively above the point at which the set of papillary muscles extend from the wall, and wherein the cardiac medical device is configured, at least in the state in which the cardiac medical device has been implanted in the left ventricle in the second configuration of the plurality of elastic arms, to cause a physical coupling position or physical coupling positions between at least a second portion of the at least one flexible cross-member expansion limiter and a second set of at least some of the plurality of elastic arms to be relatively below the point at which the set of papillary muscles extend from the wall.

22. The cardiac medical device of claim 21 wherein the cardiac medical device is configured, at least in the state in which the cardiac medical device has been implanted in the left ventricle in the second configuration of the plurality of elastic arms, to cause the physical coupling position or positions between the at least the first portion of the at least one flexible cross-member expansion limiter and the first set of at least some of the plurality of elastic arms to be relatively above the point at which the set of papillary muscles extend from the wall without the at least the first portion of the at least one flexible cross-member expansion limiter interfering with a number of chordae tendineae.

23. The cardiac medical device of claim 1, wherein a first elastic arm of the plurality of elastic arms comprises a first magnetic orientation, and a second elastic arm of the plurality of elastic arms comprises a second magnetic orientation opposite the first magnetic orientation, at least the first elastic arm magnetically discernible from at least the second elastic arm based on at least the first and the second magnetic orientations of the first elastic arm and the second elastic arm.

24. The cardiac medical device of claim 1, wherein, at least in a state in which the cardiac medical device has been implanted in the left ventricle in the second configuration of the plurality of elastic arms, at least one elastic arm of the plurality of elastic arms is or are configured to physically engage and exert expansion force to the portions of the wall that forms the left ventricle by applying spring force to the portions of the wall.

25. The cardiac medical device of claim 24, wherein, at least in the state in which the cardiac medical device has been implanted in the left ventricle in the second configuration of the plurality of elastic arms, the spring force is sufficient to preload the left ventricle beyond a fully dilated position of the left ventricle.

26. The cardiac medical device of claim 1, wherein the respective 360 degree loop of each elastic arm of the at least one elastic arm of the plurality of elastic arms is located at least proximate an apex toward which the plurality of elastic arms converge.

27. A cardiac medical device, comprising:
 a plurality of flexible arms movable between a first configuration in which the cardiac medical device is sized to be implanted into a left ventricle of a heart and a second configuration in which the plurality of flexible arms are configured to physically engage portions of a wall that forms the left ventricle and exert expansion force to assist an expansion of the left ventricle during a diastolic phase of a cardiac cycle; and
 at least one coiled loop structure formed by at least one respective flexible arm of the plurality of flexible arms,
 wherein, for each coiled loop structure of the at least one coiled loop structure:
 the coiled loop structure is located at least proximate an apex of the cardiac medical device at which at least two flexible arms of the plurality of flexible arms join at least in a state in which the plurality of flexible arms are in the second configuration, and
 at least a portion of the coiled loop structure protrudes into a space bounded by a respective portion of each of the at least two flexible arms at least in the state in which the plurality of flexible arms are in the second configuration.

28. The cardiac medical device of claim 27, further comprising:
 a coupling that allows the cardiac medical device to be retrieved from the left ventricle via a catheter, the coupling located at least proximate the apex of the cardiac medical device.

29. The cardiac medical device of claim 27 wherein at least one flexible arm of the plurality of flexible arms includes a sharp barb receivable in the wall.

30. The cardiac medical device of claim 27 wherein a portion of each flexible arm of at least one flexible arm of the plurality of flexible arms includes a respective particular coiled loop structure formed between opposed ends of the flexible arm, the respective particular coiled loop structure distinct from the at least one coiled loop structure.

31. The cardiac medical device of claim 27, further comprising:
 a connector that physically couples at least some of the plurality of flexible arms to one another, the connector located at least proximate the apex of the cardiac medical device.

32. The cardiac medical device of claim 27, wherein, at least in a state in which the cardiac medical device has been implanted in the left ventricle in the second configuration of the plurality of flexible arms, at least one flexible arm of the plurality of flexible arms is or are configured to physically engage and exert expansion force to the portions of the wall that forms the left ventricle by applying spring force to the portions of the wall.

33. The cardiac medical device of claim 32, wherein, at least in the state in which the cardiac medical device has been implanted in the left ventricle in the second configuration of the plurality of flexible arms, the spring force is sufficient to preload the left ventricle beyond a fully dilated position of the left ventricle.

34. The cardiac medical device of claim 27, wherein
the plurality of flexible arms are arranged about an axis in a circumferential arrangement when the plurality of flexible arms are in the second configuration, and
the cardiac medical device further comprises at least one flexible cross-member expansion limiter physically coupled at least to a pair of non-adjacent arms of the plurality of flexible arms to limit an expansion of at least the pair of non-adjacent arms, the pair of non-adjacent arms non-adjacent along the circumferential arrangement when the plurality of flexible arms are in the second configuration, and
at least portions of the at least one flexible cross-member expansion limiter are physically coupled to at least the pair of non-adjacent arms, at a respective location on each of at least the pair of non-adjacent arms that does not vary as the plurality of flexible arms moves between the first and the second configurations, the at least the portions of the at least one flexible cross-member expansion limiter physically coupled to at least the pair of non-adjacent arms while bypassing an adjacent arm adjacent a first arm of the pair of non-adjacent arms along the circumferential arrangement when the plurality of flexible arms are in the second configuration.

35. The cardiac medical device of claim 34 wherein
the portions of the at least one flexible cross-member expansion limiter include a first portion physically coupled to the first arm of the pair of non-adjacent arms at a first location,
the portions of the at least one flexible cross-member expansion limiter include a second portion physically coupled to a second arm of the pair of non-adjacent arms at a second location, and
the first arm of the pair of non-adjacent arms is free from any coupling to the adjacent arm at the first location.

36. The cardiac medical device of claim 34 wherein the portions of the at least one flexible cross-member expansion limiter are physically coupled to at least the pair of non-adjacent arms at a same respective location on each of at least the pair of non-adjacent arms when the plurality of flexible arms are in each of the first and the second configurations.

37. The cardiac medical device of claim 34 wherein the at least one flexible cross-member expansion limiter comprises a first elongated cross-member physically coupled to a first pair of non-adjacent arms of the plurality of flexible arms non-adjacent along the circumferential arrangement when the plurality of flexible arms are in the second configuration, and a second elongated cross-member physically coupled to a second pair of non-adjacent arms of the plurality of flexible arms non-adjacent along the circumferential arrangement when the plurality of flexible arms are in the second configuration, the second pair of non-adjacent arms different than the first pair of non-adjacent arms, the first elongated cross-member and the second elongated cross-member fixedly joined together at a cross-over point where the first and the second elongated cross-members cross each other.

38. The cardiac medical device of claim 34 wherein the at least one flexible cross-member expansion limiter comprises a first elongated cross-member physically coupled to a first pair of flexible arms of the plurality of flexible arms, the first pair of flexible arms adjacent one another along the circumferential arrangement when the plurality of flexible arms are in the second configuration.

39. The cardiac medical device of claim 38 wherein the at least one flexible cross-member expansion limiter comprises a second elongated cross-member physically coupled to a second pair of flexible arms of the plurality of flexible arms, the second pair of flexible arms different than the first pair of flexible arms, the second pair of flexible arms opposed to one another across the circumferential arrangement when the plurality of flexible arms are in the second configuration.

40. The cardiac medical device of claim 39 wherein the cardiac medical device is configured, at least in a state in which the cardiac medical device has been implanted in the left ventricle in the second configuration of the plurality of flexible arms, to cause each flexible arm of a first set of at least some of the plurality of flexible arms to contact respective portions of the wall at locations spaced relatively above a point at which a set of papillary muscles extend from the wall, and to cause the second elongated cross-member to be arranged with respect to the first elongated cross-member such that the point at which the set of papillary muscles extend from the wall is between the first and the second elongated cross members.

41. The cardiac medical device of claim 34 wherein the cardiac medical device is configured, at least in a state in which the cardiac medical device has been implanted in the left ventricle in the second configuration of the plurality of flexible arms, to cause each flexible arm of the plurality of flexible arms to contact respective portions of the wall at locations spaced relatively above a point at which a set of papillary muscles extend from the wall, and to cause a physical coupling position or physical coupling positions between at least a first portion of the at least one flexible cross-member expansion limiter and a first set of at least some of the plurality of flexible arms to be relatively above the point at which the set of papillary muscles extend from the wall, and wherein the cardiac medical device is configured, at least in the state in which the cardiac medical device has been implanted in the left ventricle in the second configuration of the plurality of flexible arms, to cause a physical coupling position or physical coupling positions between at least a second portion of the at least one flexible cross-member expansion limiter and a second set of at least some of the plurality of flexible arms to be relatively below the point at which the set of papillary muscles extend from the wall.

42. The cardiac medical device of claim 41 wherein the cardiac medical device is configured, at least in the state in which the cardiac medical device has been implanted in the left ventricle in the second configuration of the plurality of flexible arms, to cause the physical coupling position or positions between the at least the first portion of the at least one flexible cross-member expansion limiter and the first set of at least some of the plurality of flexible arms to be relatively above the point at which the set of papillary muscles extend from the wall without the at least the first portion of the at least one flexible cross-member expansion limiter interfering with a number of chordae tendineae.

43. The cardiac medical device of claim 34 wherein the cardiac medical device is configured, at least in a state in which the cardiac medical device has been implanted in the left ventricle in the second configuration of the plurality of flexible arms, to cause each flexible arm of a set of at least some of the plurality of flexible arms to contact respective portions of the wall at locations spaced relatively above a point at which a set of papillary muscles extend from the wall, and to cause physical coupling positions between at least a portion of the at least one flexible cross-member expansion limiter and at least two flexible arms of the plurality of flexible arms to be relatively above the point at which the set of papillary muscles extend from the wall.

44. The cardiac medical device of claim 43 wherein the cardiac medical device is configured, at least in the state in which the cardiac medical device has been implanted in the left ventricle in the second configuration of the plurality of flexible arms, to cause the physical coupling positions between the at least the portion of the at least one flexible cross-member expansion limiter and the at least two flexible arms to be relatively above the point at which the set of papillary muscles extend from the wall without the at least the portion of the at least one flexible cross-member expansion limiter interfering with the set of papillary muscles or with a number of chordae tendineae.

45. The cardiac medical device of claim 34 wherein the plurality of flexible arms are made of a polymeric material.

46. The cardiac medical device of claim 34 wherein the flexible cross-member expansion limiter is spaced relatively inwardly from distal ends of the plurality of flexible arms when the plurality of flexible arms are in the second configuration.

47. The cardiac medical device of claim 27 wherein the plurality of flexible arms is configurable to be delivered by a catheter.

48. The cardiac medical device of claim 27 wherein the plurality of flexible arms are made of a flexible metal wire material.

49. The cardiac medical device of claim 27 wherein the plurality of flexible arms comprise a biologically beneficial coating.

* * * * *